(12) United States Patent
Yuda et al.

(10) Patent No.: US 6,815,430 B1
(45) Date of Patent: Nov. 9, 2004

(54) GENE EXPRESSION BASE SEQUENCES FOR THERAPEUTIC USE AND DRUGS FOR GENE THERAPY

(75) Inventors: Kazuhiro Yuda, Tsukuba (JP); Katsuhiko Akiyama, Tsukuba (JP); Takeshi Goto, Tsukuba (JP); Katsuyuki Hamada, Matsuyama (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/958,021
(22) PCT Filed: Mar. 31, 2000
(86) PCT No.: PCT/JP00/02102
§ 371 (c)(1),
(2), (4) Date: Jan. 7, 2002
(87) PCT Pub. No.: WO00/60068
PCT Pub. Date: Oct. 12, 2000

(30) Foreign Application Priority Data

Apr. 2, 1999 (JP) .......................................... 11-096358

(51) Int. Cl.⁷ .......................... C07H 21/04; A01N 43/04
(52) U.S. Cl. ...................... 514/44; 536/24.1; 435/320.1
(58) Field of Search .......................... 536/24.1; 514/44; 435/320.1

(56) References Cited

U.S. PATENT DOCUMENTS

| | | | |
|---|---|---|---|
| 5,728,379 A | * | 3/1998 | Martuza et al. ............. 424/93.2 |
| 6,025,195 A | | 2/2000 | Sandig et al. |
| 6,103,527 A | | 8/2000 | Graulich et al. |

FOREIGN PATENT DOCUMENTS

| EP | 0 893 493 A2 | 7/1998 |
|---|---|---|
| GB | 2 305 920 A | 4/1997 |
| JP | 9-28378 | 2/1997 |
| WO | WO 96/34969 | 11/1996 |

OTHER PUBLICATIONS

Schneider et al (Proc. Nat. Acad. Sci. USA 92(8):3147–3151, 1995).*
Sakaguchi et al (Biochim. Biophys. Acta 1444: 111–116, 1999).*
Nakagawa et al (J. Biol. Chem. 272(26): 16688–16699, 1997).*
Carroll et al (Proc. Nat Acad. Sci. USA 90: 10270–10274, 1993.*
Leask et al (Proc. Nat. Acad. Sci. USA 88:7948–7952, 1991).*
Hamada et al., 'Molecular Cloning of Human Squamous Cell Carcinoma Antigen 1 Gene and Characterization of its Promoter', Biochimica et Biophysica Acta, 1518 (2001) pp. 124–131.

* cited by examiner

Primary Examiner—Dave T. Nguyen
Assistant Examiner—Richard Schnizer
(74) Attorney, Agent, or Firm—Fitch, Even, Tabin & Flannery

(57) ABSTRACT

The base sequence for the expression of a therapeutic gene and the medicament for gene therapy are disclosed. There is also disclosed the base sequence for the expression of a therapeutic gene, said sequence being shown in any one of from (a) to (d) and capable of directing the expression of the therapeutic gene specifically to squamous epithelium:
 (a) the base sequence set forth in SEQ ID NO:1 in the Sequence Listing;
 (b) the base sequence set forth in SEQ ID NO:18 in the Sequence Listing;
 (c) the base sequence set forth in SEQ ID NO:17 in the Sequence Listing; and
 (d) the base sequence set forth in SEQ ID NO:16 in the Sequence Listing.

Moreover, there is disclosed the medicament for gene therapy containing a therapeutic gene downstream any of the above-mentioned base sequences, capable of directing the expression of the therapeutic gene specifically to squamous epithelium.

6 Claims, 5 Drawing Sheets

SEQUENCE LISTING

<160> NUMBER OF SEQ ID NOS: 32

<210> SEQ ID NO 1
<211> LENGTH: 4324
<212> TYPE: DNA
<213> ORGANISM: HOMO SAPIENS

<400> SEQUENCE: 1

```
ttttattagt gatttcaaaa ggagagggag tgtacgaata gagtgtgggt cacagagatc      60
acgtgcttca caaggtgata gaatatcaca aggcaaatgg aggcagggtg agatcacagg     120
accacaggac ctgggtgaaa ttaaaattgc taatgaagtt tcgggcacgc attgtcattg     180
ataacatctt atcaggagac agggtttgag agcagacaac cggtctgacc aaaaatttat     240
tagatgggac tttcctcatc ctaataagcc taggagcgct acgggaggtt ggggcttatt     300
tcatccctac agcttcaacc ataaaagacg gctgccccc aaagcggcca ttttaaaggc      360
ctaccctcag gggcatattc tctttctcag ggatgttcct tgatgagaaa aagaattcag     420
```

-continued

```
cgatatttct cccatttgct tttgaaagaa gagaaatatg gctctgttcc acccagctca    480
ccggcggtca gagtttaagg ttatcactca tgttccctga acattgctgt tatcctgttc    540
tttttttcaag gtgcccagat ttcatattgt tcaaacacac atgctctaca aataatttat   600
gcagttaatg caatcatcac agggtcctgg gaccacatac attctcctca gcttgcaaag    660
atgatgggat taagagatta aagtaaagac aggcatagga aatcacaagg gtattgattg    720
aggaagtgat aagtgttcat gaaatcttca caatttatgt tcagagattg cagtaaagac    780
aggcataaga aattataaaa gtattaattt ggggaactaa taaatgtcca tgaaaacttc    840
ataatctatg ttcttctgcc atggcttcag ccagtccctc ggttcagggt ccctgacttc    900
ctgcaacata catgtgagac tatttcccgc tctgcttttc aaaccttact ggagttgttt    960
tccctcatga aaactaagaa aggaaagcta gttaatctta ttctgaggtt gttcaatata   1020
tacatattca catctgtaga aagatccttg ggaatacagt aattggcata tattctgtta   1080
tttgatgctt gaaaaatctc ttccactaac cagtttccct atagataggc acaagcacat   1140
aggtaagaaa caataaataa atgttctctt taatttgtaa cttcacaatg ctgagaaaac   1200
tttacagcct tcataaggaa gtgaggtcca ggaaaatcta ggagatattt gttaaccaac   1260
ctataaagac attagtaatg acaggatatt tcctgaaagt gtaatttccc attgaggatt   1320
tgttttttaat ttctggattc ctggatccaa tgaagttggc ataggtttat gaaatgccaa   1380
gatacataag ttggcaagtg ttcacatgca aaaaacttct tggaattcct gagctctctg   1440
tggcaatata tgacatcagg atatgtccca tctcgcacat caggatatgt cctgtcaaga   1500
atgtctatca catgccagga gtacttttta ggaacagaaa aaaatgtctg aaatggtttc   1560
tcatttgaac tcatccaagc tttctctaaa tttaagcaaa ctcctggtca ttttcagtta   1620
gtacctttcc tcaagttcaa ccttcatgac aaacctcagc atctcagaag atttagccat   1680
agtctgaaat tctcttccat agactggtcc cctgtaatcc cagtttgcct cagcttgtta   1740
tcctgctttt tattccctc tattcccagg ctgagcttct tgcttctgtc ctatgagacg    1800
ttagattcct tcactttggt acccaagtaa acccatcctt ctccatatac aggaaggtcc   1860
atttttctct tacagccctg gatgcagact cagctaagaa gaccattatt cattttggga   1920
attcttcatc taggatattt cctcttgttt ctttctctcc tatctttgag cttttttagat  1980
catcaacacc ccattagtct attacccaac ttaaatcagg gaacttatac ctcccaaact   2040
cattcagaga ctccaaacat atatattgat acaggagacc taagaagagc atgtcttggg   2100
ggttgaggaa acaggcaggt gagaaacttc cagattggaa acacagcttc ctttctcccg   2160
tccagcccct acttcatcct atctgttttcc ggaaccttgt tgtagatgaa tctcccttga   2220
cttcatgatg tgctgagaaa acaaactcat ggctggtgtt aaaaagggcc catgacaata   2280
ccaagtgttg gggagaatgt ggagaaatca gaactctatt cacagtcggt tggaatgcac   2340
acttgtgcag aattctatgg agaagagtct ggcatttcct caaaatgtta acctggattt   2400
accatatgac ccagcgattt cattcatagg tttatactca aaagaaatga agaaatatgc   2460
catgcaaaaa aatgtacatg aaaagtcaaa acatcattat tcataatagt aaatggatgg   2520
aaacaacaca aatgtccatc aacttatgaa taaagaaaat gtggtctatt catagaatgg   2580
aatattattc gaccacaaaa aggaatgatg tactgatcca tgcaatgacg tggacaaacc   2640
ttgaagataa tactagatga agaagccaa tcacaaaagg acttactgta tgattcgatt    2700
tacgtgaaat gtttagaata ggcaaatcca tagaaacagg aggtagatta ctggtttcca   2760
```

-continued

```
gggtctcgag taagggaaga acgagataca agttttcttt tggaggtagt gaaattgttg    2820
tggaacgaga tcatgatggt gatagcacaa ctttgtgaat ataataaaat cattgaattg    2880
tacagttgaa tttgtggcat ataaattata tgttaaaaaa gggggtccac aaaacaaaca    2940
gccccccact ctggttgtca gggagatatt ggattaaatg gccttggaca caaccctct    3000 ccctggccac agacattctt cagattacaa gatattccag aggaaacact ggaatgagtc    3060
tgaagccagg tgctaaatgg aaggaccacc aagaaacgtt gtgatcctga caggtcaagc    3120
aacttctttt tctgcttaat ttttaaatga aaaattagaa agctgacatt caaaatggcc    3180
cgtctgtttc aattgctctt ctcagtgtca gcctgttaac tcaatgtgtt agtctgtttt    3240
catgctgctg ataaagacat acctgagatt aggaagtaaa agaggtttaa ttggacttag    3300
agttccacgt gattggggag gcctcagaat cacggtagga ggcaaaagtt attcttacat    3360
ggtggctgca agagaaaatg aggaagaagc aaaagaagaa acccctaata aacccattgg    3420
atctcctgag acttattaac tatcatgaga atagcacaag aaagaccggc ccccatgatt    3480
caattacctc tacctgggtc cctccaacaa catgtggaaa ttctggtaga tacaattcaa    3540
gttgagattt gggtgggaac acagccaaac catatcactc agcaaggcag ataactttct    3600
cactgagcct atgcaacaga aaccatctg ggatggttgt aaggggcaca ggaagtgact    3660
ggtaggatca ctgccaaagc tgagcattca ggagaaggca atagaatcct attctccata    3720
gtatgctata agatactgaa gtacacttct tcactatctc tttggactta gaattagcac    3780
tatattcctt gttatacaga aaaattacta aggaaattca taggatgaca aaaactttca    3840
gaactgaaaa acaggaaatg taagcttttt agttctttgg tattcgaagt atgcctaaaa    3900
gacaatgcaa aatccaagaa aagaatggtg gggttttgt ttgtttgttt ttgttttgt    3960 tttacagctg gagtagaata caaagggatg gagttgaaac aaatgagagg aaattggaat    4020
tctaaactta ttctcattgg cattagaaag gcacctacat gtatttcaca tgagccggtg    4080
actgctgact tgcattctta ttttttccct atagattaaa aaggaggtac aatggtagaa    4140
ctgtaatcct gtcctttgtc ataaattttc gtattcataa aggtgagtgt tagcccgctt    4200
gtgaaatctg aagttgagta acttcaaata ctaaccacag agggagaggc agcaagagga    4260
gaggcataaa ttcaggatct cacccttcat tccacagaca cacatagcct ctctgcccac    4320
ctct                                                                  4324
```

<210> SEQ ID NO 2
<211> LENGTH: 165
<212> TYPE: DNA
<213> ORGANISM: HOMO SAPIENS

<400> SEQUENCE: 2

```
tgaattcact cagtgaagcc aacaccaagt tcatgttcga tctgttccaa cagttcagaa     60
aatcaaaaga gaacaacatc ttctattccc ctatcagcat cacatcagca ttagggatgg    120
tcctcttagg agccaaagac aacactgcac aacaaattag caagg                    165
```

<210> SEQ ID NO 3
<211> LENGTH: 19
<212> TYPE: DNA
<213> ORGANISM: Artificial Sequence
<220> FEATURE:
<223> OTHER INFORMATION: PRIMER

<400> SEQUENCE: 3

```
tgaattcact cagtgaagc                                                   19
```

<210> SEQ ID NO 4
<211> LENGTH: 19
<212> TYPE: DNA
<213> ORGANISM: Artificial Sequence
<220> FEATURE:
<223> OTHER INFORMATION: PRIMER

<400> SEQUENCE: 4
ccttgctaat ttgttgtgc                                                    19

<210> SEQ ID NO 5
<211> LENGTH: 5279
<212> TYPE: DNA
<213> ORGANISM: HOMO SAPIENS

<400> SEQUENCE: 5
ttttattagt gatttcaaaa ggagagggag tgtacgaata gagtgtgggt cacagagatc        60
acgtgcttca caaggtgata gaatatcaca aggcaaatgg aggcagggtg agatcacagg       120
accacaggac ctgggtgaaa ttaaaattgc taatgaagtt tcgggcacgc attgtcattg       180
ataacatctt atcaggagac agggtttgag agcagacaac cggtctgacc aaaaatttat       240
tagatgggac tttcctcatc ctaataagcc taggagcgct acgggaggtt ggggcttatt       300
tcatccctac agcttcaacc ataaaagacg gctgccccccc aaagcggcca ttttaaaggc       360
ctaccctcag gggcatattc tctttctcag ggatgttcct tgatgagaaa agaattcag       420 cgatatttct cccatttgct tttgaaagaa gagaaatatg gctctgttcc acccagctca       480
ccggcggtca gagtttaagg ttatcactca tgttccctga acattgctgt tatcctgttc       540 tttttttcaag gtgcccagat ttcatattgt tcaaacacac atgctctaca ataatttat       600 gcagttaatg caatcatcac agggtcctgg gaccacatac attctcctca gcttgcaaag       660
atgatgggat taagagatta agtaaagac aggcatagga aatcacaagg gtattgattg       720
aggaagtgat aagtgttcat gaaatcttca caatttatgt tcagagattg cagtaaagac       780
aggcataaga aattataaaa gtattaattt ggggaactaa taaatgtcca tgaaaacttc       840
ataatctatg ttcttctgcc atggcttcag ccagtccctc ggttcagggt ccctgacttc       900
ctgcaacata catgtgagac tatttcccgc tctgcttttc aaaccttact ggagttgttt       960
tccctcatga aaactaagaa aggaaagcta gttaatctta ttctgaggtt gttcaatata      1020
tacatattca catctgtaga aagatccttg ggaatacagt aattggcata tattctgtta      1080
tttgatgctt gaaaaatctc ttccactaac cagtttccct atagataggc acaagcacat      1140
aggtaagaaa caataaataa atgttctctt taatttgtaa cttcacaatg ctgagaaaac      1200
tttacagcct tcataaggaa gtgaggtcca ggaaaatcta ggagatattt gttaaccaac      1260
ctataaagac attagtaatg acaggatatt tcctgaaagt gtaatttccc attgaggatt      1320
tgtttttaat ttctggattc ctggatccaa tgaagttggc ataggtttat gaaatgccaa      1380
gatacataag ttggcaagtg ttcacatgca aaaaacttct tggaattcct gagctctctg      1440
tggcaatata tgacatcagg atatgtccca tctcgcacat caggatatgt cctgtcaaga      1500
atgtctatca catgccagga gtactttta ggaacagaaa aaaatgtctg aaatggtttc      1560
tcatttgaac tcatccaagc tttctctaaa tttaagcaaa ctcctggtca ttttcagtta      1620
gtacctttcc tcaagttcaa ccttcatgac aaacctcagc atctcagaag atttagccat      1680
agtctgaaat tctcttccat agactggtcc cctgtaatcc cagtttgcct cagcttgtta      1740

-continued

```
tcctgctttt tattccccctc tattcccagg ctgagcttct tgcttctgtc ctatgagacg    1800
ttagattcct tcactttggt acccaagtaa acccatcctt ctccatatac aggaaggtcc    1860
atttttctct tacagccctg gatgcagact cagctaagaa gaccattatt cattttttgga   1920
attcttcatc taggatattt cctcttgttt ctttctctcc tatctttgag cttttttagat  1980
catcaacacc ccattagtct attacccaac ttaaatcagg gaacttatac ctcccaaact    2040
cattcagaga ctccaaacat atatattgat acaggagacc taagaagagc atgtcttggg    2100
ggttgaggaa acaggcaggt gagaaacttc cagattggaa acacagcttc ctttctcccg    2160
tccagcccct acttcatcct atctgttttcc ggaaccttgt tgtagatgaa tctcccttga   2220
cttcatgatg tgctgagaaa acaaactcat ggctggtgtt aaaaagggcc catgacaata    2280
ccaagtgttg gggagaatgt ggagaaatca gaactctatt cacagtcggt tggaatgcac    2340
acttgtgcag aattctatgg agaagagtct ggcatttcct caaatgttaa acctggattt    2400
accatatgac ccagcgattt cattcatagg tttatactca aaagaaatga gaaatatgc     2460
catgcaaaaa aatgtacatg aaaagtcaaa acatcattat tcataatagt aaatggatgg    2520
aaacaacaca aatgtccatc aacttatgaa taaagaaaat gtggtctatt catagaatgg    2580
aatattattc gaccacaaaa aggaatgatg tactgatcca tgcaatgacg tggacaaacc    2640
ttgaagataa tactagatga aagaagccag tcacaaaagg acttactgta tgattcgatt    2700
tacgtgaaat gtttagaata ggcaaatcca tagaaacagg aggtagatta ctggtttcca    2760
gggtctcgag taagggaaga acgagataca agttttcttt tggaggtagt gaaattgttg    2820
tggaacgaga tcatgatggt gatagcacaa ctttgtgaat ataataaaat cattgaattg    2880
tacagttgaa tttgtggcat ataaattata tgttaaaaaa gggggtccac aaaacaaaca    2940
gccccccact ctggttgtca gggagatatt ggattaaatg gccttggaca caacccctct    3000
ccctggccac agacattctt cagattacaa gatattccag aggaaacact ggaatgagtc    3060
tgaagccagg tgctaaatgg aaggaccacc aagaaacgtt gtgatcctga caggtcaagc    3120
aacttctttt tctgcttaat ttttaaatga aaaattagaa agctgacatt caaaatggcc    3180
cgtctgtttc aattgctctt ctcagtgtca gcctgttaac tcaatgtgtt agtctgtttt    3240
catgctgctg ataaagacat acctgagatt aggaagtaaa agaggtttaa ttggacttag    3300
agttccacgt gattggggag gcctcagaat cacggtagga ggcaaaagtt attcttacat    3360
ggtggctgca agagaaaatg aggaagaagc aaaagaagaa accctaata aacccattgg     3420
atctcctgag acttattaac tatcatgaga atagcacaag aaagaccggc ccccatgatt    3480
caattacctc tacctgggtc cctccaacaa catgtggaaa ttctggtaga tacaattcaa    3540
gttgagattt gggtgggaac acagccaaac catatcactc agcaaggcag ataactttct    3600
cactgagcct atgcaacaga aaccatctg ggatggttgt aaggggcaca ggaagtgact     3660
ggtaggatca ctgccaaagc tgagcattca ggagaaggca atagaatcct attctccata    3720
gtatgctata agatactgaa gtacacttct tcactatctc tttggactta gaattagcac    3780
tatattcctt gttatacaga aaattacta aggaaattca taggatgaca aaactttca     3840
gaactgaaaa acaggaaatg taagcttttt agttctttgg tattcgaagt atgcctaaaa    3900
gacaatgcaa aatccaagaa aagaatggtg gggtttttgt ttgtttgttt ttgttttttgt   3960
tttacagctg gagtagaata caaagggatg gagttgaaac aaatgagagg aaattggaat    4020
tctaaactta ttctcattgg cattagaaag gcacctacat gtatttcaca tgagccggtg    4080
actgctgact tgcattctta ttttttccct atagattaaa aaggaggtac aatggtagaa    4140
```

-continued

```
ctgtaatcct gtcctttgtc ataaattttc gtattcataa aggtgagtgt tagcccgctt      4200
gtgaaatctg aagttgagta acttcaaata ctaaccacag agggagaggc agcaagagga      4260
gaggcataaa ttcaggatct caccttcat tccacagaca cacatagcct ctctgcccac       4320
ctctgcttcc tctaggaaca caggtaagag cttcaagcct ctccagctta ataacatgaa      4380
ttatttttga gaataataat gatactgtgt tctatatcat gcatctcctg cattctgtct      4440
gattatattt tacttattct gccagagcaa aattaaaata cctatttcat ctgatttgtc      4500
ctttatctaa attgcttagt tccaagtaaa ccaaggcact tttaggaaca cagagggaga      4560
gtgccttgca gccagagagt cttgaaggag atgtcaggga cgcatcttaa cagctggttg      4620
gatgtgatcc acagaggtct cctgttagca ttcattgtaa agccttccta cctagcccta      4680
gtgtagccag caatgaagga agagggtct attacttatt tacagtagtc tttaaaaaca       4740
ctaattttgt gaggcttcta attaagacat taatatattt aatatatgca cattgtagaa      4800
agattgaaac gttaaaaata agatgaggaa aactttaaat gtcaaaatct cacaacacag      4860
atatataatt tctttaagaa aattgtacta caaaatacca ttccatttat taaagtcatt      4920
ctgacaggaa tctgatgctt ttccaggagt tccagatcac atcgagttca ccatgaattc      4980
actcagtgaa gccaacacca agttcatgtt cgacctgttc caacagttca cgaaaatcaa      5040
aagagaacaa catcttctat tccctatca gcatcacatc agcattaggg atggtcctct       5100
taggagccaa agacaacact gcacaacaga ttaagaaggt agctatcagc atcattatgt      5160
tgtcctgttg cagttttct ctggttccgt cggctagcac gcagatggta atagatgtgg       5220
tggtctgatg ggtagcacag ggggctgagc aggaattccc gtaactgtga gaccactgg      5279
```

<210> SEQ ID NO 6
<211> LENGTH: 4384
<212> TYPE: DNA
<213> ORGANISM: Artificial Sequence
<220> FEATURE:
<223> OTHER INFORMATION: TEMPLATE

<400> SEQUENCE: 6

```
gatcaagggg catgcagcca tcggggaaaa tccatagtgc agataaagca aggaggaaga       60
agaaggacag ttctagtaaa agggagaaca tcaatatagg atgtttctta gcaatagaaa      120
aagaaggcca agaggaatta gggagagagt tataagagat cagcaagggg acagggttag      180
atttggtttg gtttgaaagc atacagtaaa tatgatgtct gtccctggca gtgttggcag      240
agtaggaagg aggaagggag gcaagagata atatcatttt ctctgtgctc caactgtact      300
tacatatgag actatttccc tctctgcttt tcaaacctta ctggagttgt tttccctcat      360
gaaaaccaag aaaggaaagc tagttagtct tgttctgagg ttgttcaatg tatacatatc      420
tatatctgta gacagaatcc ttgggaatac agtaattgac atatattctg ttatttgatg      480
cttgaaaaat ctcctccact aaccagtttc cctatagatt gccacaagca cataataaga      540
aacaataaat aaaatgttct cttgactttg ttacttaaca atgctgagaa aactttacag      600
ccttcataag gaagtgaggt ccaggaaaat ctaggagata tttcttaacc aatctataaa      660
ggcattagta atgacaggat atttcctgaa agtgtaattt cccattgagg atttgttttt      720
aatttctgga ttcctggagc caatgaagtt ggtgtatgtt tatgaaatat caagagacat      780
aagttggcaa gtgttcatat gcaaaaactt cttggaatttt ctgagttctc tgtggcaata      840
tatgacatca ggatatgtcc agtctcacac accaggatat gtcctttcta gcctgtctat      900
```

-continued

```
cacatgctag gagaactatt taggaacaga aaaaaatgcc tgaaatgatt tctcatttga    960
actcatccaa gctttctcta aatttaagca aactcctggt catttttcagt tagtaccttt   1020 ccttaagttc aaccttcagg gcaaacctcc gtgcctcaga cgtttagcca tagtctgaaa   1080
ttctcttcca tagattggtc ccctgtaacc ccggtttgtc tcagcttgtt atcctgtttt   1140
tttcttccct ccattcccag gatgagcttg ttgcttctgt cctatgagac attagattcc   1200
ttttctttgg tacccgagta aatccatcct actccaatag aggaaggtcc attttttgtct  1260 tatagcgctg gatgcagact cagctgagaa gaccattatt catttttgga attctttatc   1320
tcagatattt cctcttcttt cttttttcttc tatctttgga tttttagtcc atcaacgccc   1380
cattagtcta ttccccgact tcaatcaggg aacttatacc tcttaaactc attcagagac   1440
tcaaaacata tatattgata caggagacct aagaagagca tgtcttgggg gttgaggaaa   1500
caggcaggtg agaaatttcc agattggaaa cacagcttcc tttctcccat ccagccccta   1560 cttttcagcct atgtgtttct ggcaccttgt tgtagataaa tctcccttga ctttgtgatg   1620
tgctgagaaa acaaactcac ggctggtgtt aaaaagggcc catgacaata ccaagtgttg   1680
gggagaatgt ggagaaatca gaactctatt cacggtcggt tggaatgcac acttgtgcag   1740
aattctatgg agaagagtct ggcatttcct caaaatgtta acctggattt accatatgac   1800
ccagcgattt cattcatagg tttatactca aagaaatga agaaatatgc catgcaaaaa   1860
aatgtacatg aaaggtcaca acatcattat tcataatagt aaaaggatgg aaacaacaca   1920
aatgtccatc aacttatgat taagaaaat ctggtctatt catagaatgg aatattattc   1980
gaccacaaaa aggaatgatg tactgatcca tgcaatgatg tggacaaacc atgaaaataa   2040
cactagatta aagaagccag tcacaaaagg acttactgta tgattccatt tacctgaaat   2100
gtttggaata ggcaaatcca tagaaacagg aggtagattc ctggtttcca gggtctccag   2160
gaagggaaga atgaagtaca agatttcttt tggaggtagt gaaattgttg tggaatgaga   2220
tcatgatgat gatagcacaa ctttgtgaat ataataaaat cattgaattg tacagttgaa   2280
tttatggtat ataaattata tgttaataaa aaggggggtcc acaaaacaaa cagccccccca   2340 ctctggttgt cagggagata ttggattaaa tggccttgga caacaacccc tctccctggc   2400
cacagacatt cttcagatta caagatattc caggggaaac actggaatga gtctgaagcc   2460
aggtgctaaa cagaaggacc attgagaaat gttgtgatcc tgacaggtca agcaatttat   2520
ttttcggctt catttttaaa tgtaaaatta gaaagctgcc atttaaaatg gcccgtctgt   2580
ttcaattgct cttctcagtg tcagcctgtt aactcaatgt gttagtctgt tttcatgctg   2640
ctgataaaaa cataccgtag actggcaaga aaaagaggtt taattgggct tagagttcca   2700
cgtgattggg gaggcctcag aatcacagta ggaggcaaaa gttattctta catggtggct   2760
gcaagagaag atgaggaaga agcaaaagaa gaaaccctg ataaacccat cggatctcct   2820
gaggcttatt aactatcatg agaatagcac aagaaagacc ggcccccatg attcaattac   2880
ctctacctgg gtccctccaa taacatgtgg aaattctggt agatacaatt caagttgaga   2940
tttgggtggg aacacagcca aaccatatca ctcagcaagg cagataactt tctcactgag   3000
cctatgcaac agaaaaccat ctgggatggt tgtaaggggc acaggaagtg actggtagga   3060
tcactgccaa agctgagcac tcaggagaag gcaatagaat cctattctcc atagtatgct   3120
ataagatact gaagtacact tcttcactat ctctttggac ttagaattag cactacattc   3180
cttgttatac agaaaaatta ctaaggaaat tcataggatg acaaaaactt tcagaactga   3240
aaaacaggaa atgtaagctt tttagttctt tggtattcga agtatgccta aaagacaatg   3300
```

```
caaaatccaa gaaaagaatg gtggggtttt tgtttgtttg gttttgtttt tgttttacag    3360
ctggagtaga atacaaaggg atggagttga acaaatgag aggaaattgg aattctaaac     3420
ttattctcat tggcattaga aaggcaccta catgtatttc acatgagccg gtgactgctg    3480
acttgcattc ttatttttc cctatagatt aaaaaggagg tacaatggta gaactgtaat    3540
cctgtccttt gtcataaatt ttcatattca taaaggtgag tgttagcccg cttgtgaaat    3600
ctgaagttga gtaacttcaa atactaacca cagagggaaa ggcagcaaga ggagaggcat    3660
aaatttagga tctcacccctt cattccacag acacacacag cctctctgcc cacctctgct   3720
tcctctagga acacaggtaa gagcttcaag cctctccagc ttaataacat gaattatttt    3780
tgagaataat aatgatactg tgttctatat catgcatctc ctgcattctg tctgattata    3840
ttttacttat tctgccagag caaaattaaa atacctattt catctgattt gtcctttatc    3900
taaattgctt agttccaagt aaaccaaggc acttttagga acacagaggg agagtgcctt    3960
gcagccagag agtcttgaag gagatgtcag ggacgcatct taacagctgg ttggatgtga    4020
tccacagagg tctcctgtta gcattcattg taaagccatc ctaccagct ctagtgtaac    4080 cagcaatgaa agaaagataa agagggtcga ttacttattt acaatagtct ttaaaaacgt    4140
agttttgtaa gccttctaat taggacatta atatatttaa tatatgcaca ttgtagaaag    4200
attgaagcgt taaaaataag agaaaaactt taaatgtcaa aatctcacaa cccagatata    4260
tcatttcttt aagaaaattg tactacaaaa taccattcca tttattaaag tcattctgac    4320
aggaatctga tgcttttcca ggagttccag atcacatcga gttcaccatg aattcactca    4380
gtga                                                                 4384
```

<210> SEQ ID NO 7
<211> LENGTH: 30
<212> TYPE: DNA
<213> ORGANISM: Artificial Sequence
<220> FEATURE:
<223> OTHER INFORMATION: PRIMER

<400> SEQUENCE: 7
aagcagtggt aacaacgcag agtacgcggg                                     30

<210> SEQ ID NO 8
<211> LENGTH: 23
<212> TYPE: DNA
<213> ORGANISM: Artificial Sequence
<220> FEATURE:
<223> OTHER INFORMATION: PRIMER

<400> SEQUENCE: 8
aagcagtggt aacaacgcag agt                                            23

<210> SEQ ID NO 9
<211> LENGTH: 19
<212> TYPE: DNA
<213> ORGANISM: Artificial Sequence
<220> FEATURE:
<223> OTHER INFORMATION: PRIMER

<400> SEQUENCE: 9
ccagatagca cgagaccgc                                                 19

<210> SEQ ID NO 10
<211> LENGTH: 29
<212> TYPE: DNA

```
<213> ORGANISM: Artificial Sequence
<220> FEATURE:
<223> OTHER INFORMATION: PRIMER

<400> SEQUENCE: 10
cccacgcgtc cggtgactgc tgacttgca                                29

<210> SEQ ID NO 11
<211> LENGTH: 29
<212> TYPE: DNA
<213> ORGANISM: Artificial Sequence
<220> FEATURE:
<223> OTHER INFORMATION: PRIMER

<400> SEQUENCE: 11
cccacgcgta tgacaaaaac tttcagaac                                29

<210> SEQ ID NO 12
<211> LENGTH: 29
<212> TYPE: DNA
<213> ORGANISM: Artificial Sequence
<220> FEATURE:
<223> OTHER INFORMATION: PRIMER

<400> SEQUENCE: 12
cccacgcgtc agaatcacgg taggaggca                                29

<210> SEQ ID NO 13
<211> LENGTH: 29
<212> TYPE: DNA
<213> ORGANISM: Artificial Sequence
<220> FEATURE:
<223> OTHER INFORMATION: PRIMER

<400> SEQUENCE: 13
cccacgcgtg gttggaatgc acacttgtg                                29

<210> SEQ ID NO 14
<211> LENGTH: 29
<212> TYPE: DNA
<213> ORGANISM: Artificial Sequence
<220> FEATURE:
<223> OTHER INFORMATION: PRIMER

<400> SEQUENCE: 14
cccacgcgtt cctcagcttg caaagatga                                29

<210> SEQ ID NO 15
<211> LENGTH: 29
<212> TYPE: DNA
<213> ORGANISM: Artificial Sequence
<220> FEATURE:
<223> OTHER INFORMATION: PRIMER

<400> SEQUENCE: 15
cccagatcta gaggtgggca gagaggcta                                29

<210> SEQ ID NO 16
<211> LENGTH: 250
<212> TYPE: DNA
<213> ORGANISM: HOMO SAPIENS

<400> SEQUENCE: 16
ccggtgactg ctgacttgca ttcttatttt ttccctatag attaaaaagg aggtacaatg    60
gtagaactgt aatcctgtcc tttgtcataa attttcgtat tcataaaggt gagtgttagc   120
```

-continued

| | |
|---|---|
| ccgcttgtga aatctgaagt tgagtaactt caaatactaa ccacagaggg agaggcagca | 180 |
| agaggagagg cataaattca ggatctcacc cttcattcca cagacacaca tagcctctct | 240 |
| gcccacctct | 250 |

<210> SEQ ID NO 17
<211> LENGTH: 500
<212> TYPE: DNA
<213> ORGANISM: HOMO SAPIENS

<400> SEQUENCE: 17

| | |
|---|---|
| atgacaaaaa ctttcagaac tgaaaaacag gaaatgtaag cttttttagtt ctttggtatt | 60 |
| cgaagtatgc ctaaaagaca atgcaaaatc caagaaaaga atggtggggt ttttgtttgt | 120 |
| ttgttttttgt ttttgtttta cagctggagt agaatacaaa gggatggagt tgaaacaaat | 180 |
| gagaggaaat tggaattcta aacttattct cattggcatt agaaaggcac ctacatgtat | 240 |
| ttcacatgag ccggtgactg ctgacttgca ttcttatttt ttccctatag attaaaaagg | 300 |
| aggtacaatg gtagaactgt aatcctgtcc tttgtcataa attttcgtat tcataaaggt | 360 |
| gagtgttagc ccgcttgtga aatctgaagt tgagtaactt caaatactaa ccacagaggg | 420 |
| agaggcagca agaggagagg cataaattca ggatctcacc cttcattcca cagacacaca | 480 |
| tagcctctct gcccacctct | 500 |

<210> SEQ ID NO 18
<211> LENGTH: 1000
<212> TYPE: DNA
<213> ORGANISM: HOMO SAPIENS

<400> SEQUENCE: 18

| | |
|---|---|
| cagaatcacg gtaggaggca aaagttattc ttacatggtg gctgcaagag aaaatgagga | 60 |
| agaagcaaaa gaagaaaccc ctaataaacc cattggatct cctgagactt attaactatc | 120 |
| atgagaatag cacaagaaag accggccccc atgattcaat tacctctacc tgggtccctc | 180 |
| caacaacatg tggaaattct ggtagataca attcaagttg agatttgggt gggaacacag | 240 |
| ccaaaccata tcactcagca aggcagataa ctttctcact gagcctatgc aacagaaaac | 300 |
| catctgggat ggttgtaagg ggcacaggaa gtgactggta ggatcactgc caaagctgag | 360 |
| cattcaggag aaggcaatag aatcctattc tccatagtat gctataagat actgaagtac | 420 |
| acttcttcac tatctctttg gacttagaat tagcactata ttccttgtta tacagaaaaa | 480 |
| ttactaagga aattcatagg atgacaaaaa ctttcagaac tgaaaaacag gaaatgtaag | 540 |
| cttttttagtt ctttggtatt cgaagtatgc ctaaaagaca atgcaaaatc caagaaaaga | 600 |
| atggtggggt ttttgtttgt ttgttttttgt ttttgtttta cagctggagt agaatacaaa | 660 |
| gggatggagt tgaaacaaat gagaggaaat tggaattcta aacttattct cattggcatt | 720 |
| agaaaggcac ctacatgtat ttcacatgag ccggtgactg ctgacttgca ttcttatttt | 780 |
| ttccctatag attaaaaagg aggtacaatg gtagaactgt aatcctgtcc tttgtcataa | 840 |
| attttcgtat tcataaaggt gagtgttagc ccgcttgtga aatctgaagt tgagtaactt | 900 |
| caaatactaa ccacagaggg agaggcagca agaggagagg cataaattca ggatctcacc | 960 |
| cttcattcca cagacacaca tagcctctct gcccacctct | 1000 |

<210> SEQ ID NO 19
<211> LENGTH: 1997
<212> TYPE: DNA

<213> ORGANISM: HOMO SAPIENS

<400> SEQUENCE: 19

```
ggttggaatg cacacttgtg cagaattcta tggagaagag tctggcattt cctcaaaatg      60
ttaacctgga tttaccatat gacccagcga tttcattcat aggtttatac tcaaaagaaa     120
tgaagaaata tgccatgcaa aaaaatgtac atgaaaagtc aaaacatcat tattcataat     180
agtaaatgga tggaaacaac acaaatgtcc atcaacttat gaataaagaa aatgtggtct     240
attcatagaa tggaatatta ttcgaccaca aaaaggaatg atgtactgat ccatgcaatg     300
acgtggacaa accttgaaga taatactaga tgaaagaagc cagtcacaaa aggacttact     360
gtatgattcg atttacgtga atgtttaga ataggcaaat ccatagaaac aggaggtaga     420
ttactggttt ccagggtctc gagtaaggga agaacgagat acaagttttc ttttggaggt     480
agtgaaattg ttgtggaacg agatcatgat ggtgatagca caactttgtg aatataataa     540
aatcattgaa ttgtacagtt gaatttgtgg catataaatt atatgttaaa aaggggggtc     600
cacaaaacaa acagcccccc actctggttg tcagggagat attggattaa atggccttgg     660
acaacaaccc tctccctggc cacagacatt cttcagatta caagatattc cagaggaaac     720
actggaatga gtctgaagcc aggtgctaaa tggaaggacc accaagaaac gttgtgatcc     780
tgacaggtca agcaacttct ttttctgctt aattttttaaa tgaaaaatta gaaagctgac     840
attcaaaatg gcccgtctgt ttcaattgct cttctcagtg tcagcctgtt aactcaatgt     900
gttagtctgt tttcatgctg ctgataaaga catacctgag attaggaagt aaaagaggtt     960
taattggact tagagttcca cgtgattggg gaggcctcag aatcacggta ggaggcaaaa    1020
gttattctta catggtggct gcaagagaaa atgaggaaga agcaaaagaa gaaacccccta    1080
ataaacccat tggatctcct gagacttatt aactatcatg agaatagcac aagaaagacc    1140
ggccccccatg attcaattac ctctacctgg gtccctccaa caacatgtgg aaattctggt    1200
agatacaatt caagttgaga tttgggtggg aacacagcca aaccatatca ctcagcaagg    1260
cagataactt tctcactgag cctatgcaac agaaaaccat ctgggatggt tgtaagggggc    1320
acaggaagtg actggtagga tcactgccaa agctgagcat tcaggagaag gcaatagaat    1380
cctattctcc atagtatgct ataagatact gaagtacact tcttcactat ctctttggac    1440
ttagaattag cactatattc cttgttatac agaaaaatta ctaaggaaat tcataggatg    1500
acaaaaactt tcagaactga aaaacaggaa atgtaagctt tttagttctt tggtattcga    1560
agtatgccta aaagacaatg caaaatccaa gaaaagaatg gtgggttttt tgtttgtttg    1620
ttttttgtttt tgttttacag ctggagtaga atacaaaggg atggagttga aacaaatgag    1680
aggaaattgg aattctaaac ttattctcat tggcattaga aaggcaccta catgtatttc    1740
acatgagccg gtgactgctg acttgcattc ttatttttttc cctatagatt aaaaaggagg    1800
tacaatggta gaactgtaat cctgtccttt gtcataaatt ttcgtattca taaaggtgag    1860
tgttagcccg cttgtgaaat ctgaagttga gtaacttcaa atactaacca cagagggaga    1920
ggcagcaaga ggagaggcat aaattcagga tctcacccct cattccacag acacacatag    1980
cctctctgcc cacctct                                                   1997
```

<210> SEQ ID NO 20
<211> LENGTH: 3680
<212> TYPE: DNA
<213> ORGANISM: HOMO SAPIENS

<400> SEQUENCE: 20

-continued

```
tcctcagctt gcaaagatga tgggattaag agattaaagt aaagacaggc ataggaaatc      60
acaagggtat tgattgagga agtgataagt gttcatgaaa tcttcacaat ttatgttcag     120
agattgcagt aaagacaggc ataagaaatt ataaaagtat taatttgggg aactaataaa     180
tgtccatgaa aacttcataa tctatgttct tctgccatgg cttcagccag tccctcggtt     240
cagggtccct gacttcctgc aacatacatg tgagactatt tcccgctctg cttttcaaac     300
cttactggag ttgttttccc tcatgaaaac taagaaagga aagctagtta atcttattct     360
gaggttgttc aatatataca tattcacatc tgtagaaaga tccttgggaa tacagtaatt     420
ggcatatatt ctgttatttg atgcttgaaa aatctcttcc actaaccagt ttccctatag     480
ataggcacaa gcataggt aagaaacaat aaataaatgt tctctttaat ttgtaacttc      540
acaatgctga gaaaacttta cagccttcat aaggaagtga ggtccaggaa aatctaggag     600
atatttgtta accaacctat aaagacatta gtaatgacag atatttcct gaaagtgtaa     660 tttcccattg aggatttgtt tttaatttct ggattcctgg atccaatgaa gttggcatag     720
gtttatgaaa tgccaagata cataagttgg caagtgttca catgcaaaaa acttcttgga     780
attcctgagc tctctgtggc aatatatgac atcaggatat gtcccatctc gcacatcagg     840
atatgtcctg tcaagaatgt ctatcacatg ccaggagtac ttttt aggaa cagaaaaaaa     900 tgtctgaaat ggtttctcat ttgaactcat ccaagctttc tctaaattta agcaaactcc     960
tggtcatttt cagttagtac ctttcctcaa gttcaacctt catgacaaac ctcagcatct    1020
cagaagattt agccatagtc tgaaattctc ttccatagac tggtcccctg taatcccagt    1080
ttgcctcagc ttgttatcct gcttttt att cccctctatt cccaggctga gcttcttgct    1140
tctgtcctat gagacgttag attccttcac tttggtaccc aagtaaaccc atccttctcc    1200
atatacagga aggtccattt ttctcttaca gccctggatg cagactcagc taagaagacc    1260
attattcatt tttggaattc ttcatctagg atatttcctc ttgtttcttt ctctcctatc    1320
tttgagcttt ttagatcatc aacaccccat tagtctatta cccaacttaa atcagggaac    1380
ttatacctcc caaactcatt cagagactcc aaacatatat attgatacag gagacctaag    1440
aagagcatgt cttgggggtt gaggaaacag gcaggtgaga aacttccaga ttggaaacac    1500
agcttccttt ctcccgtcca gcccctactt catcctatct gtttccggaa ccttgttgta    1560
gatgaatctc ccttgacttc atgatgtgct gagaaaacaa actcatggct ggtgttaaaa    1620
agggcccatg acaataccaa gtgttgggga gaatgtggag aaatcagaac tctattcaca    1680
gtcggttgga atgcacactt gtgcagaatt ctatggagaa gagtctggca tttcctcaaa    1740
atgttaacct ggatttacca tatgacccag cgatttcatt cataggttta tactcaaaag    1800
aaatgaagaa atatgccatg caaaaaaatg tacatgaaaa gtcaaaacat cattattcat    1860
aatagtaaat ggatggaaac aacacaaatg tccatcaact tatgaataaa gaaaatgtgg    1920
tctattcata gaatggaata ttattcgacc acaaaaagga atgatgtact gatccatgca    1980
atgacgtgga caaaccttga agataatact agatgaaaga agccagtcac aaaaggactt    2040
actgtatgat tcgatttacg tgaaatgttt agaataggca aatccataga aacaggaggt    2100
agattactgg tttccagggt ctcgagtaag ggaagaacga gatacaagtt ttcttttgga    2160
ggtagtgaaa ttgttgtgga acgagatcat gatggtgata gcacaacttt gtgaatataa    2220
taaaatcatt gaattgtaca gttgaattg tggcatataa attatatgtt aaaaaagggg     2280
gtccacaaaa caaacagccc cccactctgg ttgtcaggga gatattggat taaatggcct    2340
```

```
tggacaacaa ccctctccct ggccacagac attcttcaga ttacaagata ttccagagga    2400
aacactggaa tgagtctgaa gccaggtgct aaatggaagg accaccaaga aacgttgtga    2460
tcctgacagg tcaagcaact tcttttttctg cttaattttt aaatgaaaaa ttagaaagct   2520
gacattcaaa atggcccgtc tgtttcaatt gctcttctca gtgtcagcct gttaactcaa    2580
tgtgttagtc tgttttcatg ctgctgataa agacatacct gagattagga agtaaaagag    2640
gtttaattgg acttagagtt ccacgtgatt ggggaggcct cagaatcacg gtaggaggca    2700
aaagttattc ttacatggtg gctgcaagag aaaatgagga agaagcaaaa gaagaaaccc    2760
ctaataaacc cattggatct cctgagactt attaactatc atgagaatag cacaagaaag    2820
accggccccc atgattcaat tacctctacc tgggtccctc caacaacatg tggaaattct    2880
ggtagataca attcaagttg agatttgggt gggaacacag ccaaaccata tcactcagca    2940
aggcagataa ctttctcact gagcctatgc aacagaaaac catctgggat ggttgtaagg    3000
ggcacaggaa gtgactggta ggatcactgc caaagctgag cattcaggag aaggcaatag    3060
aatcctattc tccatagtat gctataagat actgaagtac acttcttcac tatctctttg    3120
gacttagaat tagcactata ttccttgtta tacagaaaaa ttactaagga aattcatagg    3180
atgacaaaaa ctttcagaac tgaaaaacag gaaatgtaag cttttttagtt ctttggtatt    3240 cgaagtatgc ctaaaagaca atgcaaaatc caagaaaaga atggtggggt ttttgtttgt    3300 ttgttttttgt ttttgtttta cagctggagt agaatacaaa gggatggagt tgaaacaaat    3360
gagaggaaat tggaattcta aacttattct cattggcatt agaaaggcac ctacatgtat    3420
ttcacatgag ccggtgactg ctgacttgca ttcttatttt ttccctatag attaaaaagg    3480
aggtacaatg gtagaactgt aatcctgtcc tttgtcataa attttcgtat tcataaaggt    3540
gagtgttagc ccgcttgtga aatctgaagt tgagtaactt caaatactaa ccacagaggg    3600
agaggcagca agaggagagg cataaattca ggatctcacc cttcattcca cagacacaca    3660
tagcctctct gcccacctct                                                3680
```

<210> SEQ ID NO 21
<211> LENGTH: 29
<212> TYPE: DNA
<213> ORGANISM: Artificial Sequence
<220> FEATURE:
<223> OTHER INFORMATION: PRIMER
<400> SEQUENCE: 21
cccacgcgtt gtgaaatctg aagttgagt                                       29

<210> SEQ ID NO 22
<211> LENGTH: 29
<212> TYPE: DNA
<213> ORGANISM: Artificial Sequence
<220> FEATURE:
<223> OTHER INFORMATION: PRIMER
<400> SEQUENCE: 22
cccacgcgta atagaatcct attctccat                                       29

<210> SEQ ID NO 23
<211> LENGTH: 29
<212> TYPE: DNA
<213> ORGANISM: Artificial Sequence
<220> FEATURE:
<223> OTHER INFORMATION: PRIMER
<400> SEQUENCE: 23

```
cccacgcgtt cactcagcaa ggcagataa                                      29
```

```
<210> SEQ ID NO 24
<211> LENGTH: 125
<212> TYPE: DNA
<213> ORGANISM: HOMO SAPIENS

<400> SEQUENCE: 24
tgtgaaatct gaagttgagt aacttcaaat actaaccaca gagggagagg cagcaagagg    60
agaggcataa attcaggatc tcacccttca ttccacagac acacatagcc tctctgccca   120
cctct                                                              125

<210> SEQ ID NO 25
<211> LENGTH: 625
<212> TYPE: DNA
<213> ORGANISM: HOMO SAPIENS

<400> SEQUENCE: 25
aatagaatcc tattctccat agtatgctat aagatactga agtacacttc ttcactatct    60
ctttggactt agaattagca ctatattcct tgttatacag aaaaattact aaggaaattc   120
ataggatgac aaaaactttc agaactgaaa acaggaaat gtaagctttt tagttctttg   180
gtattcgaag tatgcctaaa agacaatgca aaatccaaga aaagaatggt ggggttttttg   240 tttgtttgtt tttgttttttg tttttacagct ggagtagaat acaaagggat ggagttgaaa   300
caaatgagag gaaattggaa ttctaaactt attctcattg cattagaaa ggcacctaca   360 tgtatttcac atgagccggt gactgctgac ttgcattctt attttttccc tatagattaa   420
aaaggaggta caatggtaga actgtaatcc tgtcctttgt cataaatttt cgtattcata   480
aaggtgagtg ttagcccgct tgtgaaatct gaagttgagt aacttcaaat actaaccaca   540
gagggagagg cagcaagagg agaggcataa attcaggatc tcacccttca ttccacagac   600
acacatagcc tctctgccca cctct                                        625

<210> SEQ ID NO 26
<211> LENGTH: 750
<212> TYPE: DNA
<213> ORGANISM: HOMO SAPIENS

<400> SEQUENCE: 26
tcactcagca aggcagataa ctttctcact gagcctatgc aacagaaaac catctgggat    60
ggttgtaagg ggcacaggaa gtgactggta ggatcactgc caaagctgag cattcaggag   120
aaggcaatag aatcctattc tccatagtat gctataagat actgaagtac acttcttcac   180
tatctctttg gacttagaat tagcactata ttccttgtta tacagaaaaa ttactaagga   240
aattcatagg atgacaaaaa ctttcagaac tgaaaacag gaaatgtaag cttttagtt   300 ctttggtatt cgaagtatgc ctaaaagaca atgcaaaatc caagaaaaga atggtggggt   360
ttttgtttgt ttgtttttgt ttttgtttta cagctggagt agaatacaaa gggatggagt   420
tgaaacaaat gagaggaaat tggaattcta aacttattct cattggcatt agaaaggcac   480
ctacatgtat ttcacatgag ccggtgactg ctgacttgca ttcttattt ttccctatag   540 attaaaaagg aggtacaatg gtagaactgt aatcctgtcc tttgtcataa attttcgtat   600
tcataaaggt gagtgttagc ccgcttgtga aatctgaagt tgagtaactt caaatactaa   660
ccacagaggg agaggcagca agaggagagg cataaattca ggatctcacc cttcattcca   720
```

| cagacacaca tagcctctct gcccacctct | 750 |

<210> SEQ ID NO 27
<211> LENGTH: 125
<212> TYPE: DNA
<213> ORGANISM: HOMO SAPIENS

<400> SEQUENCE: 27

| tgtgaaatct gaagttgagt aacttcaaat actaaccaca gagggaaagg cagcaagagg | 60 |
| agaggcataa atttaggatc tcaccttca ttccacagac acacatagcc tctctgccca | 120 |
| cctct | 125 |

<210> SEQ ID NO 28
<211> LENGTH: 250
<212> TYPE: DNA
<213> ORGANISM: HOMO SAPIENS

<400> SEQUENCE: 28

| ccggtgactg ctgacttgca ttcttatttt ttccctatag attaaaaagg aggtacaatg | 60 |
| gtagaactgt aatcctgtcc tttgtcataa attttcatat tcataaaggt gagtgttagc | 120 |
| ccgcttgtga aatctgaagt tgagtaactt caaatactaa ccacagaggg aaaggcagca | 180 |
| agaggagagg cataaattta ggatctcacc cttcattcca cagacacaca tagcctctct | 240 |
| gcccacctct | 250 |

<210> SEQ ID NO 29
<211> LENGTH: 500
<212> TYPE: DNA
<213> ORGANISM: HOMO SAPIENS

<400> SEQUENCE: 29

| atgacaaaaa cttcagaac tgaaaaacag gaaatgtaag cttttagtt ctttggtatt | 60 |
| cgaagtatgc ctaaaagaca atgcaaaatc caagaaaaga atggtggggt ttttgtttgt | 120 |
| ttggttttgt ttttgtttta cagctggagt agaatacaaa gggatggagt tgaaacaaat | 180 |
| gagaggaaat tggaattcta aacttattct cattggcatt agaaaggcac ctacatgtat | 240 |
| ttcacatgag ccggtgactg ctgacttgca ttcttatttt ttccctatag attaaaaagg | 300 |
| aggtacaatg gtagaactgt aatcctgtcc tttgtcataa attttcatat tcataaaggt | 360 |
| gagtgttagc ccgcttgtga aatctgaagt tgagtaactt caaatactaa ccacagaggg | 420 |
| aaaggcagca agaggagagg cataaattta ggatctcacc cttcattcca cagacacaca | 480 |
| tagcctctct gcccacctct | 500 |

<210> SEQ ID NO 30
<211> LENGTH: 625
<212> TYPE: DNA
<213> ORGANISM: HOMO SAPIENS

<400> SEQUENCE: 30

| aatagaatcc tattctccat agtatgctat aagatactga agtacacttc ttcactatct | 60 |
| ctttggactt agaattagca ctacattcct tgttatacag aaaaattact aaggaaattc | 120 |
| ataggatgac aaaactttc agaactgaaa acaggaaat gtaagcttt tagttctttg | 180 |
| gtattcgaag tatgcctaaa agacaatgca aaatccaaga aagaatggt ggggttttg | 240 |
| tttgtttggt tttgtttttg ttttacagct ggagtagaat acaaagggat ggagttgaaa | 300 |
| caaatgagag gaaattggaa ttctaaactt attctcattg gcattagaaa ggcacctaca | 360 |

```
tgtatttcac atgagccggt gactgctgac ttgcattctt attttttccc tatagattaa      420
aaaggaggta caatggtaga actgtaatcc tgtcctttgt cataaatttt catattcata      480 aagtgagtg ttagcccgct tgtgaaatct gaagttgagt aacttcaaat actaaccaca       540
gagggaaagg cagcaagagg agaggcataa atttaggatc tcacccttca ttccacagac      600
acacatagcc tctctgccca cctct                                            625

<210> SEQ ID NO 31
<211> LENGTH: 750
<212> TYPE: DNA
<213> ORGANISM: HOMO SAPIENS

<400> SEQUENCE: 31
tcactcagca aggcagataa ctttctcact gagcctatgc aacagaaaac catctgggat      60
ggttgtaagg ggcacaggaa gtgactggta ggatcactgc caaagctgag cactcaggag      120
aaggcaatag aatcctattc tccatagtat gctataagat actgaagtac acttcttcac      180
tatctctttg gacttagaat tagcactaca ttccttgtta tacagaaaaa ttactaagga      240
aattcatagg atgacaaaaa ctttcagaac tgaaaacag gaaatgtaag cttttagtt        300 ctttggtatt cgaagtatgc ctaaaagaca atgcaaaatc caagaaaaga atggtggggt     360
ttttgtttgt ttggttttgt ttttgtttta cagctggagt agaatacaaa gggatggagt     420
tgaaacaaat gagaggaaat tggaattcta aacttattct cattggcatt agaaaggcac     480
ctacatgtat ttcacatgag ccggtgactg ctgacttgca ttcttatttt ttccctatag     540
attaaaaagg aggtacaatg gtagaactgt aatcctgtcc tttgtcataa attttcatat     600
tcataaaggt gagtgttagc ccgcttgtga aatctgaagt tgagtaactt caaatactaa     660
ccacagaggg aaaggcagca agaggagagg cataaattta ggatctcacc cttcattcca     720
cagacacaca tagcctctct gcccacctct                                       750

<210> SEQ ID NO 32
<211> LENGTH: 1001
<212> TYPE: DNA
<213> ORGANISM: HOMO SAPIENS

<400> SEQUENCE: 32
cagaatcacg gtaggaggca aaagttattc ttacatggtg gctgcaagag aagatgagga      60
agaagcaaaa gaagaaaccc ctgataaacc catcggatct cctgaggctt attaactatc      120
atgagaatag cacaagaaag accggccccc atgattcaat tacctctacc tgggtccctc      180
caataacatg tggaaattct ggtagataca attcaagttg agatttgggt gggaacacag      240
ccaaaccata tcactcagca aggcagataa ctttctcact gagcctatgc aacagaaaac      300
catctgggat ggttgtaagg ggcacaggaa gtgactggta ggatcactgc caaagctgag      360
cactcaggag aaggcaatag aatcctattc tccatagtat gctataagat actgaagtac      420
acttcttcac tatctctttg gacttagaat tagcactaca ttccttgtta tacagaaaaa      480
ttactaagga aattcatagg atgacaaaaa ctttcagaac tgaaaacag gaaatgtaag       540 cttttagtt ctttggtatt cgaagtatgc ctaaaagaca atgcaaaatc caagaaaaga      600
atggtggggt ttttgtttgt ttggttttgt ttttgtttta cagctggagt agaatacaaa     660
gggatggagt tgaaacaaat gagaggaaat tggaattcta aacttattct cattggcatt    720
agaaaggcac ctacatgtat ttcacatgag ccggtgactg ctgacttgca ttcttatttt    780
```

-continued

```
ttccctatag attaaaaagg aggtacaatg gtagaactgt aatcctgtcc tttgtcataa    840
attttcatat tcataaaggt gagtgttagc ccgcttgtga aatctgaagt tgagtaactt    900
caaatactaa ccacagaggg aaaggcagca agaggagagg cataaattta ggatctcacc    960
cttcattcca cagacacaca tagcctctct sgcccacctc t                      1001
```

GENE EXPRESSION BASE SEQUENCES FOR THERAPEUTIC USE AND DRUGS FOR GENE THERAPY

This application is the National phase of International Application PCT/JP00/02102, filed Mar. 31, 2000, which designated the U.S.

TECHNICAL FIELD

This invention relates to base sequences capable of directing the expression of therapeutic genes specifically to squamous epithelia, and to medicaments for gene therapy capable of directing the expression of therapeutic genes specifically to squamous epithelia by the use of the base sequences.

BACKGROUND ART

Gene therapy is a therapeutic method by which genes or cells having the introduced genes are administered to the human body for the purpose of the treatment of diseases, and it has drawn attention as a new modality which may replace those currently in use. In 1990 gene therapy was performed on two children who had congenial severe combined immunodeficiency resulting from adenosine deaminase (ADA) deficiency in the United States. Since then over 2,100 cases of gene therapy had been performed around the world till the end of 1996. In this country, the first gene therapy on an ADA deficient patient was initiated in August of 1995.

In the research of gene therapy an indispensable technique is to devise an improvement in the safety of medicaments for gene therapy; for example, targeting with which therapeutic genes are only introduced (transferred) into cells that are the subject of treatment not only increases the effectiveness by preventing the administered vector for gene therapy from uselessly diffusing, but also decreases the expression of exogenous genes in unwanted organs or tissues, which then makes it an indispensable technique.

Specifically, there are techniques disclosed among others: a HIV vector that is patterned after human immunodeficiency virus (HIV) utilizes the propensity of its envelope protein (existing on the surface) specifically binding to CD4 protein, and can transfer genes only into CD4 positive cells (Shimada T. et al., J. Clin. Invest., 88, 1043, 1991); a recombinant viral vector derived by modifying the envelope of Moloney murine leukemia virus with heregulin can transfer genes only into cells such as lung cancer cells that overexpress epidermal growth factor receptor (EGFR) (Han X. L., et al., Proc. Natl. Acad. Sci. USA, 92, 21, 9747, 1995); a folate conjugated to poly-L-lysine having enhanced affinity to cancer cells which relies on the fact that the folate receptor is overexpressd in cancer cells (Gottschalk S., et al., Gene Ther., 1, 3, 185, 1994; Lee R. J., Hung L., J. Biol. Chem., 271, 14, 8481, 1996).

In the meantime, the development of a system capable of directing the expression of a gene specifically to a tissue which is the subject of treatment (tissue specific expression system) is under way. The tissue specific expression system is a technique that focuses on a protein which is only expressed in a certain organ or tissue and that utilizes a gene sequence regulating the expression of a gene such as a promoter and/or an enhancer for the gene that encode this protein.

This technique has been disclosed in reviews that are already in public knowledge (e.g., Gabi U. Dachs, et al., Oncology Res., 9, 313, 1997). The tissue-specific promoters/enhancers which are known include the promoter/enhancer for α-fetoprotein (AFP) the specific expression of which can be seen in hepatocellular carcinoma, the promoter region of prostate specific antigen (PSA) the expression of which is increased in prostate cancer, the von Willebrand factor (vWf) and the tie-2/tek promoter both of which are endothelial cell specific, the DF3 promoter the increased expression of which can be seen in breast cancer, the albumin enhancer that is expressed specifically in liver, the tyrosinase promoter that can be specifically expressed in melanoma cells, the myellin basic protein (MBP) promoter that is specific for glioma cells, the osteocalcin promoter that is specific for osteosarcoma cells, and the like.

The disease-specific promoters/enhancers include the promoter for carcinoembryonic antigen (CEA) the increased expression of which can be seen in many carcinomas, the HER/neu promoter exhibiting enhanced expression in breast and pancreatic cancers, and the Myc-Max response element that activates transcription by the action of the Myc protein family/Max protein complex which is implicated in cell proliferation, differentiation, and apoptosis. The promoters/enhancers the expression of which is controlled by a wide variety of conditions have also been reported, including the promoter for early growth response-1 gene (Egr-1) upon radiation, tissue type plasminogen activator (t-PA), the GRP78/BiP protein promoter that is induced by tumor-specific conditions such as glucose deprivation and anoxia, hypoxia response element (HRE) exhibiting specific expression under hypoxic conditions, and the like.

However, against squamous cell carcinomas such as uterine cervical cancer, skin cancer, head and neck cancer, esophagus cancer, and lung cancer which are reported to account for about 60% of all the carcinomas, there has been no system capable of directing the expression of genes specifically to those carcinomas: there has been no system for carrying out effective gene therapy on these squamous cell carcinomas.

DISCLOSURE OF THE INVENTION

It is an object of this invention to provide a base sequence capable of directing the expression of a therapeutic gene specifically to squamous epithelium. It is also an object of the invention to provide a medicament for gene therapy capable of directing the expression of a therapeutic gene specifically to squamous epithelium by the use of said base sequence.

As a result of having pursued diligent investigations on the above-stated problems, the present inventors found novel base sequences capable of directing the expression of therapeutic genes specifically to squamous epithelia. Further, it was found that these novel base sequences had more enhanced capability of gene expression in squamous cell carcinomas such as SKG IIIa cells than in normal squamous epithelia; and this led to the completion of this invention.

Specifically, this invention relates to a base sequence for the expression of a therapeutic gene, said sequence capable of directing the expression of the therapeutic gene specifically to squamous epithelium.

More specifically, it relates to a base sequence for the expression of a therapeutic gene, said sequence being shown in any one of from (a) to (d) and capable of directing the expression of a therapeutic gene specifically to squamous epithelium:

(a) the base sequence set forth in SEQ ID NO:1 in the Sequence Listing;

(b) the base sequence set forth in SEQ ID NO:18 in the Sequence Listing;

(c) the base sequence set forth in SEQ ID NO:17 in the Sequence Listing; and (d) the base sequence set forth in SEQ ID NO:16 in the Sequence Listing.

Also, this invention relates to a base sequence for the expression of a therapeutic gene, said sequence being shown in any one of from (a) to (d) in which one or more bases have been deleted or substituted, or to which one or more bases have been added and capable of directing the expression of a therapeutic gene specifically to squamous epithelium:

(a) the base sequence set forth in SEQ NO:1 in the Sequence Listing;

(b) the base sequence set forth in SEQ NO:18 in the Sequence Listing;

(c) the base sequence set forth in SEQ ID NO:17 in the Sequence Listing; and (d) the base sequence set forth in SEQ ID:16 in the Sequence Listing.

Further, this invention relates to a medicament for gene therapy having the base sequence for the expression of a therapeutic gene as described above and the therapeutic gene in the downstream thereof, said medicament capable of directing the expression of a therapeutic gene specifically to squamous epithelium. Still further, it encompasses a method for directing the expression of a therapeutic gene to be desirably expressed in certain squamous epithelium by the use of the medicament.

BEST MODE FOR CARRYING OUT THE INVENTION

Figure 1:
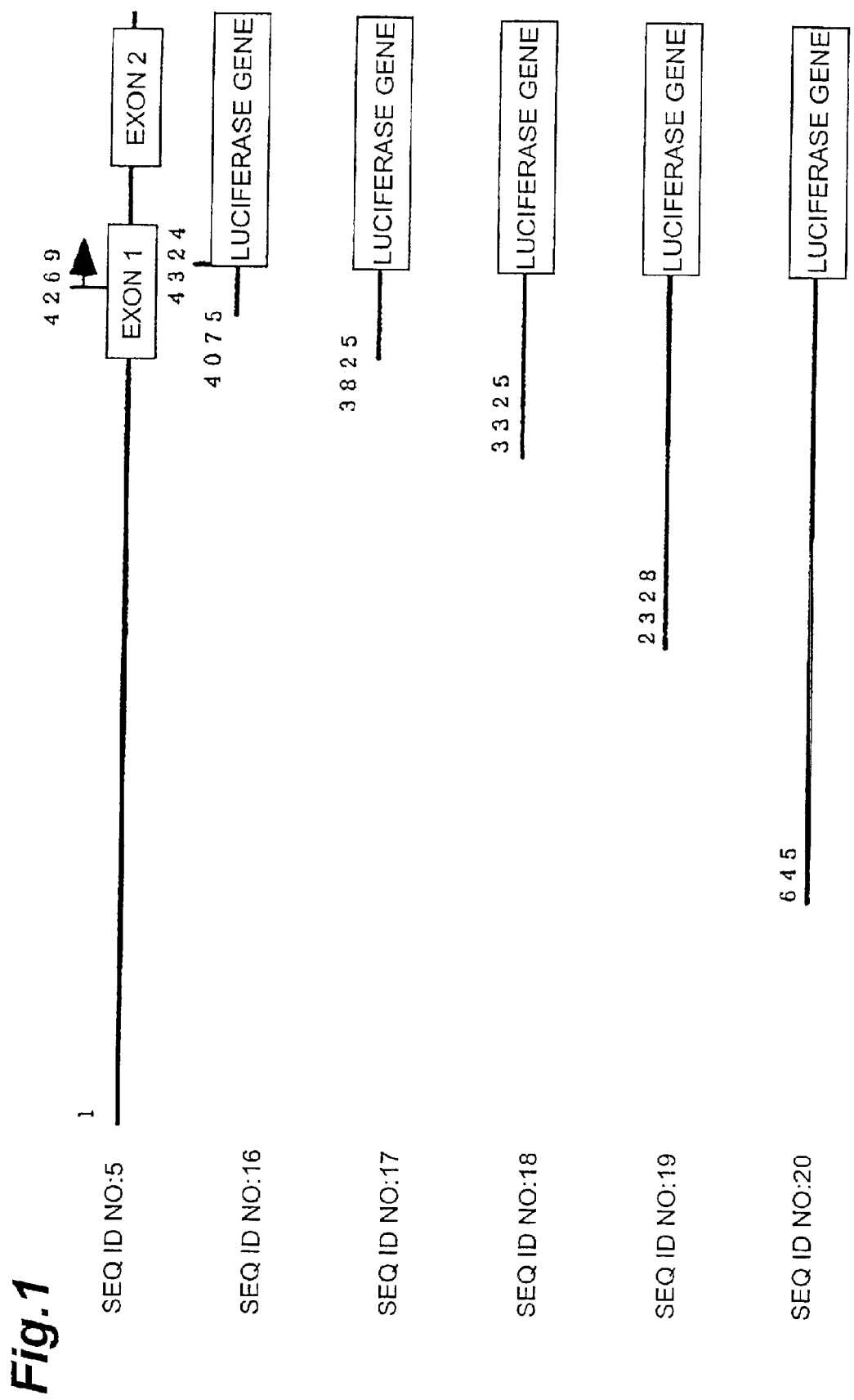
FIG. 1 is a graph showing the differences in length among inserted fragments in the upstream of SCC-A1 gene for cell species specific expression plasmids according to this invention where the arrow indicates Cap site and the numerals are those based on the base positions in SEQ ID NO:5.

This invention will be described in detail by referring to embodiments.
(Base Sequences)

The base sequences capable of directing the expression of therapeutic genes specifically to squamous epithelia according to this invention (hereafter referred to as "base sequence (s) of this invention") are consecutive base sequences in the upstream of the structural gene defining the amino acid sequence of squamous cell carcinoma antigen 1 (hereafter referred to as "SCC-A1").

This SSC-A is a protein that is widely known as a tumor marker of squamous cell carcinomas such as uterine cervical cancer, for which SCC-A1 and SCC-A2 exist that are about 95% homologous in gene sequence. These are both located at chromosomal 18q21.3 (S. S. Schneider, et al., Proc. Natl. Acad. Sci. USA, 92, 3147, 1995). Sakaguchi et al. analyzed the SCC-A2 promoter and reported that the strongest transcriptional activity of the gene expression in SKG IIIa (squamous cell carcinoma) cells was obtained when a DNA fragment with a length between the transcriptional start site and 500 bp upstream was used. (Sakaguchi Y., Biochemica et Biophysica Acta, 1444, 111–116, 1999). Shirato et al. determined the serum level of SCC-A in patients with squamous cell carcinoma who had undergone radiotherapy and, consequently, found the SCC-A level in the patients with uterine cervical cancer was correlated with its prognosis; and they reported that the SCC-A protein level would be useful for post treatment monitoring. (Shirato H., et al., Acta Oncologica 32, 6, 663, 1993). The amino acid sequence of SSC-A and the gene sequence encoding the protein are disclosed in Japanese Unexamined Appln. Publn. Hei 4-200387.

A base sequence of this invention comprises a portion or the whole of the consecutive base sequence of 4324 bp set forth in SEQ ID NO:1 and is a base sequence capable of directing the expression of a therapeutic gene specifically to squamous epithelium. Further, it comprises a portion or the whole of the consecutive base sequence of 1000 bp set forth in SEQ ID NO:18 and is a base sequence capable of directing the expression of a therapeutic gene specifically to squamous epithelium. Further, it comprises a portion or the whole of the consecutive base sequence of 500 bp set forth in SEQ ID NO:17 and is a base sequence capable of directing the expression of a therapeutic gene specifically to squamous epithelium. Still, further, it comprises a portion or the whole of the consecutive base sequence of 250 bp set forth in SEQ ID NO:16 and is a base sequence capable of directing the expression of a therapeutic gene specifically to squamous epithelium.

Furthermore, embraced by the base sequences of this invention is a base sequence derivable from any one of the foregoing base sequences by deletion, substitution or modification of one or more bases therefrom, or addition of one or more bases thereto, insofar as it has the function of directing the expression of a therapeutic gene specifically to squamous epithelium.

There are no limitations to the method of acquiring the base sequences of this invention. On the basis of the base sequences disclosed herein, methods that are known in the art are preferably applicable. Specifically, they may be prepared by conventional PCR in a buffer containing salts such as magnesium ion with appropriately adjusted concentrations, using the upstream genome region of the SCC-1 gene as a template and primers that are designed to allow amplification of the targeted region of the template DNA sequence in addition to thermostable DNA polymerase.

The thermostable DNA polymerases to be used include Taq DNA polymerase derived from *Themus aquaticus,* Pfu DNA polymerase derived from *Pyrococcus furiosus,* thermostable DNA polymerase species of the *E. coli* recombinant type, and the like. PCR may be carried out on a PCR apparatus available commercially.

The base sequence of this invention may be 100 bases or less, because it may comprise a portion of the base sequence set forth in SEQ ID NO:1, SEQ ID NO:18, SEQ ID NO:17, or SEQ ID NO:16. In this case, it is possible to synthesize the base sequences of this invention as nucleic acid compounds.

The nucleic acid compounds include oligodeoxyribonucleotides of the natural type, oligodeoxyribonucleotides of the phosphorothioate type, oligodeoxyribonucleotides of the methyl phosphonate type, oligodeoxyribonucleotides of the phosphoramidite type, oligodeoxyribonucleotides of the H-phosphonate type, oligodeoxyribonucleotides of the tri-ester type, and the like.

In addition to the above-mentioned methods, the synthesis may be carried out according to the phosphoramidite method by using a DNA/RNA synthesizer when the nucleic acid synthesis is employed.

The phosphoramidite method is a synthetic method based on the following: a phosphoramidite protected with the cyanoethyl group or the like is bound to the 3'-end of a modified deoxyribonucleotide to form a reagent; the reagent is used for condensation to the 5'-end of a different modified deoxyribonucleotide or oligo-modified deoxyribonucleotide. The synthesis is completed in the state where the protected group of sugar hydroxyl moieties at the 5'-end is in linkage at the last cycle. After a synthesized oligomer is cleaved from the support, basic portions and phosphoric acid portions are deprotected to produce crudely purified products. The crudely purified product is purified using a conventional purification method such as ethanol precipitation, or alternatively is purified by a variety of methods such as reverse phase chromatography, ion-exchange chromatography, high pressure liquid chromatography based on the principle of gel filtration chromatography, and super critical chromatography.

(Therapeutic Genes)

The base sequences of this invention are useful as promoters for directing the expression of therapeutic genes specifically to squamous epithelia.

Specifically, a therapeutic gene to be desirably expressed specifically in squamous epithelium can be placed downstream the base sequence of this invention and can be used, for example, by being inserted into a part of the viral genome sequence of a viral vector.

The therapeutic genes are not particularly limited insofar as they are those which are expected to have therapeutic effects. Such genes include, for example, XPA-XPG genes, keratin genes, collagen genes, tyrosinase genes, NF1 genes, CTLA4Ig genes, ATM genes, PLP genes, DM20 genes, GCH genes, superoxide dismutase 1 genes, ALD genes, proteolipid protein genes, KCNA1 genes, fibroblast growth factor-3, COMP genes, DSDST genes, fibrillin 1 genes, fibroblast growth factor receptor, monoamine oxidase A or B genes, ADMLX genes, androgen receptor genes, myocardial β-myosin heavy chain genes, myocardial troponin T genes, α-tropomyosin genes, myocardial myosin binding protein C genes, ventricular myosin alkaline light chain genes, ventricular myosin regulating light chain genes, myocardial troponing I genes, LQT1-4 genes, elastin genes, PKD1 and PKD2 genes, phosphatidylinositol class A genes, 1,25-(OH) 2D3 receptor genes, CLCN5 genes, erythrocyte ankyrin genes, CFTR genes, holocarboxylase synthetase genes, ATP8A and ATP8B genes, PAX3 genes, MITF genes, PAX6 genes, crystallin genes, SLC3A1 genes, WAS genes, interleukin 2 receptor γ chain genes, adenosine deaminase genes, OCRL-1 genes, RET genes, endothelin B genes, BLM genes, angiotensinogen genes, angiotensin converting enzyme genes, angiotensin II type I receptor genes, lipoprotein lipase genes, apoC-II genes, low density lipoprotein receptor genes, leptin genes, crowsaw genes, leptin receptor genes, brain glycogen phosphorylase genes, fas genes, fas ligand genes, human leukocyte antigen genes, p53 genes, p15 genes, p16 genes, tyrosinase related protein 1 and tyrosinase related protein 2 genes, VEGF genes, factor VIII genes, factor IX genes, apoE genes, apoB genes, and apoB-100 genes. On or more species of these can be combined for use.

The therapeutic genes do not need to be those derived from human if they are expected to have therapeutic effects. Such examples include thymidine kinase genes derived from human herpes simplex virus, viral viroids such as human hepatitis of δ type virus, and ribozymes derived from protozoa ciliate (e.g., Tetrahymena).

Among those mentioned above, the representative genes that are expected to be especially efficacious for squamous epithelia, for example, include any genes of from XPA to XPG that are involved in the nucleotide excision repair mechanism with respect to xeroderma pigmentosum, keratin genes or VII type collagen genes with respect to epidermolysis bullosa, thyrosinase genes with respect to thyrosinase negative type albinism, and NF1 genes with respect to neurofibroma type 1.

The representative genes that are expected to be especially efficacious for squamous cell carcinomas, for example, include suicide genes such as thymidine kinase genes derived from human herpes simplex virus, genes that encode cancer-specific antigens such as brain glycogen phosphorylase genes, genes that promote the apoptosis of fas gene or the like, genes that enhance the immunogenicity of cancer cells such as human leukocyte antigen genes, cancer-suppressing genes such as p53 gene, genes that act in an antagonistic manner on squamous cell carcinoma (e.g., antisenses and ribozymes).

This invention is also applicable in treatment for aesthetic purposes, including the inhibition of crease formation, improved humectation, the inhibition of choasma or ephelides formation, and the inhibition of being greasy and acne formation. Specifically, on or more species of the keratin gene or of the collagen gene can be combined for use to inhibit crease formation as well as to improve humectation. To inhibit choasma and ephelides formation, one or more kinds of antisense or ribozyme against a series of enzymes that are involved in melanin formation can be combined for use.

The therapeutic genes of this invention also encompass marker genes. For the marker gene, CAT, GUS, β-gal, GFP, EGFP, and the like may be used.

A poly A signal may be inserted downstream the therapeutic gene in order to regulate the stability of the expressed therapeutic gene within cell.

(Method for Introduction of Therapeutic Genes)

A therapeutic gene is introduced into the downstream of the base sequence of this invention and the therapeutic gene is delivered to normal squamous epithelia, squamous cell carcinomas, and the like: such technique is not particularly limited, and, for example, viral vectors may be used, or alternatively non-viral vectors such as synthetic polyamino acids and cationic lipids may be used.

When viral vectors are to be used, virus-derived vectors such as a retroviral vector, an adeno-associated vector, a recombinant HIV vector, and a herpes simplex virus can be employed. In the viral vector, the base sequence of this invention is used by being inserted to a part of the viral genome sequence. For example, within the retroviral vector where a leukemia viral vector is used, a recombinant viral genome may be constructed based on such a design that the Long Terminal Repeat (LTR) derived from the leukemia viral vector, the base sequence of this invention, the therapeutic gene, the poly A signal, and LTR are in sequence from the 5'-end of the virus genome. The constructed viral vectors may be packaged into virus particles by methods known in the art.

Carriers for non-viral vectors such as synthetic polyamino acids or cationic lipids are to be used: in the case of a synthetic polyamino acid, a carrier comprising an amino acid (e.g., polylysine or serine) as the principle agent may be used, while in the case of a cationic lipid, liposome or the like may be used. In the case of a non-viral vector, the base sequence of this invention, the therapeutic gene and the poly-A signal (both downstream the base sequence) may be inserted to a plasmid for use.

(Medicaments for Gene Therapy)

The medicaments for gene therapy according to this invention employ the base sequences of this invention described above and are capable of directing the expression of certain therapeutic genes specifically to squamous epithelia. This medicament for gene therapy can be obtained by using the base sequence of this invention as a promoter and introducing the therapeutic gene to the downstream thereof.

When the medicament for gene therapy is delivered to the cell by the above-mentioned method, the base sequence of this invention can direct the expression of the therapeutic gene specifically to squamous epithelium. Further, according to this invention, the therapeutic gene can be allowed for its strong expression especially in cancerated squamous epithelium.

Such effect is observed with the consecutive sequence of 4324 bases set forth in SEQ NO:1; within this sequence, it is strongly observed with the consecutive sequence of 1000 bases set forth in SEQ NO:18, with the consecutive sequence of 500 bases set forth in SEQ NO:17, and with the consecutive sequence of 250 bases set forth in SEQ NO:16.

The therapeutic effects of the medicament for gene therapy according to this invention are utilized in the genetic diseases of all tissues and organs, including squamous epithelia of skin, lung, esophagus, and uterus. Specifically, they are useful in the treatment of genetic skin diseases such as xeroderma pigmentosum, epidermolysis bullosa, ichthyosis, albinism, thyrosinase negative type albinism, and neurofibroma type 1.

They are also useful in treatment for aesthetic purposes, including the inhibition of crease formation on the skin, improvement of humectation, the inhibition of choasma or ephelides formation, and the inhibition of being greasy and acne formation.

The medicaments for gene therapy according to this invention are useful not only in the treatment of diseases of squamous epithelia, but also in the gene therapy of squamous cell carcinomas; they are especially effective for uterine cervical cancer, skin cancer, head and neck cancer, esphageal cancer, and lung cancer.

Methods for administering the medicament for gene therapy according to this invention may employ those by oral administration or parental administration, in addition to those by direct administration to the targeted tissue and organ. The oral administration includes sublingual administration. The parental administration includes injections the administration routes of which are subcutaneous, intramuscular, through vein, arterial, and through drip infusion, suppositories, ointments, and patches.

The doses for the medicament for gene therapy according to this invention differ depending on the age, the route of administration and the frequency of administration, and can appropriately be altered. In this case, an effective amount of the medicament for gene therapy according to this invention, a suitable diluent, and a pharmacologically usable carrier form a composition, which is normally administered: the effective amount is in the range of from 1 to 100,000 $\mu$g/kg and is administered continuously, or in a divided dose of one to several times daily, or once every few days.

When the medicament for gene therapy according to this invention is orally administered, tablets, granules, fine granules, powders, capsules or the like are applicable. These compositions may contain binders, inclusions, excipients, disintegrants, and the like; and they may be in any state of solution for internal use, suspension, emulsion, syrup, and others. When parental administration is used, the composition therefor may contain a stabilizer, a buffer, a preservative, an isotonic agent, and the like, and it is provided in such a state that is an ample for unit dosage, a container for multiple dosages or a tube.

The embodiments of this invention will be described concretely by referring to the examples; however, the invention is not to be limited by the following examples.

EXAMPLES

Example 1

Preparation of Membranes for Screening

Human genome DNA library (EMBL3 SP6/T7, Clonetech #HL2067j, Sau3A I partial digest; Clontech Laboratories Inc.) was diluted with a phage dilution buffer [50 mM Tris-HCl (GIBCO Inc.) containing 100 mM NaCl (Wako Pure Chemical Industries, Ltd.) and 100 mM MgSO$_4$ (Wako Pure Chemical Industries, Ltd.), pH 7.5, 0.01% gelatin] to give a phage plaque number of $1 \times 10^4$ pfu (plaque forming unit) per 100 $\mu$l, whereby a plate was prepared for the primary screening such that plaques were uniformly formed thereon. Screening was thus carried out on the total of $1.5 \times 10^5$ plaques. The phage preparation containing positive phage clones from the primary screening was diluted with the phage dilution buffer to give a phage plaque number of 3000 pfu per 100 $\mu$l, whereby a plate was prepared for the secondary screening such that the isolated plaques were formed thereon.

E. coli K802 strain had been grown in 5 ml of LB medium (DIFCO Inc.) one day before it was seeded, and 1 ml of the culture was inoculated in a 5 ml LB medium containing 0.2% maltose and 10 mM MgSO$_4$. Then, cultivation was continued until OD600 nm reached the value of 0.6; thereby, E coli was prepared to transfect a phage.

The E. coli preparation (300 $\mu$l) described above was mixed with a phage dilution and was incubated at 37° C. for 15 minutes. After having been subjected to autoclave, it was added to a LB medium containing 6 ml of 0.75% Bacto-Agar (DIFCO Inc.) incubated at 48° C. and the total amount was added to the LB agar medium. After allowing to stand at room temperature for about 20 minutes, it was incubated at 37° C. overnight.

The plate was maintained at 4° C. for 1 hour. Hybond-N+ (Amersham Pharmacia Biotech) was brought into close contact with the LB agar medium, which was allowed to stand for 1 minute. The membrane was air-dried and immersed in a Denature buffer (0.4 M NaOH solution) for 5 minutes, in a Neutralization buffer (0.5 M Tris-HCl solution containing 1 M NaCl, pH 7.5) for 5 minutes, and in 2×SSC for 5 minutes sequentially. The membrane was treated with a UV cross link (UV Strata-linker; Stratagene) and stored in a HYBRIBAG (Cosmo Bio Co., Ltd.).

Example 2

Synthesis of DNA Probe

A DNA probe derived from the SCC-A2 gene that was used for screening was prepared in the following manner. Specifically, cDNA was prepared from mRNA of human uterus cervical cancer cell line HT-III (American Type Cell Collection or ATCC) using M-MLV reverse transcriptase (GIBCO Inc.). PCR primers (SEQ ID Nos.:3 and 4) were used in PCR (GeneAmp PCR system 2400; Perkin Elmer Inc.) to synthesize a 165 bp PCR product. Purification was carried out using a QIAquick PCR purification kit (QIAGEN Inc.) to yield the DNA probe.

Example 3

Preparation of $^{32}$P-labeled DNA Probe

For the labeling of the DNA probe prepared in Example 2 with a radioisotope, a Random primer DNA labeling kit (Takara Shuzo Co., Ltd.) was used to carry out $^{32}$P labeling. Purification was carried out by using a QIAquick nucleotide removal kit (QIAGEN Inc.).

Example 4

Screening by Plaque Hybridization

To the membrane prepared in Example 1 was added a prehybridization solution (GIBCO Inc.) at 20 ml per one sheet, which was incubated at 42° C. for 2 hours. After the prehybridization solution was discarded, 20 ml of the hybridization solution (GIBCO Inc.) containing the DNA probe prepared in Example 3 ($1 \times 10^7$ cpm/ml) was added to the membrane and it was incubated at 42° C. overnight. The membrane was washed three times with 1 l of 6×SSC containing 0.1% SDS at 42° C. for 30 minutes, and twice with 1 l of 2×SSC containing 0.1% SDS at 65° C. for 30 minutes. The membrane was enclosed in a HYBRIBAG (Cosmo Bio Co., Ltd.) and exposed to an X-ray film (Fuji Film Co., Ltd.) for development at −80° C. for 3 days. The developed film and the plate were superimposed, and then the locations of positive plaques were identified. The locations of positive plaques were cut out and collected, corresponding to their agar areas, to which 500 μl of phage dilution buffer and 5 μl of chloroform (Wako Pure Chemical Industries, Ltd.) was added. After agitation with a Vortex and precipitation of gel fragments upon centrifugation, the supernatant containing positive phage particles was collected. To further isolate positive phages, a secondary screening was carried out according to the methods as described in Examples 1, 3 and the present Example. Thus two kinds of positive phage clone (B612 and C618) were isolated from the isolated plaques.

Example 5

Large-scale Preparation of Phage DNA

E. coli K802 strain had been grown one day before it was seeded until OD600 nm reached the value of 0.6.

The phage preparation obtained in Example 4 was diluted with a phage dilution buffer to adjust B612 and C618 to $10^{10}$ pfu/ml, respectively. After cultivation at 37° C., chloroform and NaCl were added to the phage preparation, which was shaken at 37° C. for 30 minutes. Centrifugation at 5000×g for 30 minutes was carried out and a supernatant containing phages was collected. Extraction of the phage DNAs was performed in the following manner. After addition of 100 g of polyethylene glycol (Wako Pure Chemical Industries, Ltd.) and precipitation overnight, super-centrifugation was conducted at 35000 rpm for 18 hours by using 0.75 g/ml of CsCl (GIBCO Inc.). Then, dialysis was carried out overnight against a SM buffer [50 mM Tris-HCl (pH 7.5), 100 mM NaCl, 10 mM $MgSO_4$, 0.01% gelatin]. After this was subjected to shaking with a phenol solution containing 0.02% SDS for 1 hour, purification was carried out by dialysis with TE buffer. This resulted in the collection of 800 μg of the phage DNA for B612 as well as in the collection of 910 μg of the phage DNA for C618.

Example 6

Sequencing of the Upstream Sequence of SCC-A Gene

In both B612 and C618 clones, sequencing was carried out on the upstream of the sequence set forth in SEQ ID NO:2.

This resulted in the DNA sequence set forth in SEQ ID NO:5 from C618 and the DNA sequence set forth in SEQ ID NO:6 from B612. The results of homology search showed that the 3'-end region of SEQ ID NO:5 was highly homologous to the exon 1 and exon 2 sequences of human squamous cell carcinoma antigen 1 (SCC-A1) and that the 3'-end region of SEQ ID NO:6 was highly homologous to the exon 1 and exon 2 sequences of human squamous cell carcinoma antigen 1 (SCC-A2). This revealed that SEQ ID NO:5 was a sequence containing the upstream of the SCC-A1 genome gene and a portion of the SCC-A1 gene and that SEQ ID NO:6 was a sequence containing the upstream of the SCC-A2 genome gene and a portion of the SCC-A2 gene.

Example 7

Determination of Cap Site

Total mRNA was prepared from SKG IIIa cells (Human Science Research Resource Bank Co., Ltd.; formerly Japan Cancer Research Resource Bank Co., Ltd.) by using ISOGEN (Nippon Gene Co., Ltd.). Reverse transcription employed a SMART PCR cDNA SYNTHESIS kit (Clontech Laboratories Inc.) and Superscript II RNase H reverse transcriptase (GIBCO Inc.). This produced cDNA where the sequence set forth in SEQ ID NO: 7 was linked to its 5'-end. This reverse transcript was used as a template in PCR, which was carried out using PCR primers of SEQ ID NO:8 (appended to the SMART PCR cDNA SYNTHESIS kit) and SEQ ID NO:9 (Sawady Technology Co., Ltd.).

The mixed solution after reaction was subjected to 0.8% agarose electrophoresis and the PCR product amplified specifically was collected as a gel fragment. The gel was extracted using a QIAquick Gel extraction kit (QIAGEN Inc.).

The purified PCR product was mixed with 0.1 μg of Bluescript 1I T-vector (Toyobo Co., Ltd.) and ligation was carried out by using T4 DNA Ligase (GIBCO Inc.) at 4° C. overnight.

Competent E. coli XLI-blue (Takara Shuzo Co., Ltd.), 200 μl, was dissolved in ice, and it was added to the ligation reaction solution described above and maintained for 30 minutes.

After incubation at 42° C. for 60 seconds, it was again placed in ice for 5 minutes. To this was added 800 μl of a SOC medium (GIBCO Inc.) and incubated at 37° C. for 1 hour. Cells (100 μl) were inoculated in a LB agar medium containing 50 μg/ml ampicilin (Wako Pure Chemical Industries, Co., Ltd.) and incubated at 37° C. overnight. Single colonies (five clones) were selected and were added to a LB liquid medium containing 50 μg/ml ampicilin, which was further incubated at 37° C. overnight.

The five clone plasmids that had been picked up were purified with a QIAGEN plasmid MINI kit (QIAGEN Inc.).

The upstream sequence of the five purified clones was identified with a DNA sequencer Type 310 (ABI Inc.).

The result revealed that the Cap site of the SCC-A1 gene was the 4296th base in SEQ ID NO:5.

Example 8

Construction (I) of Expression Plasmids

The phage DNA (C618) obtained in Example 5 was used as a template in PCR, which was carried out using combinations of PCR primers shown in Table 1 to prepare five DNA fragments in the upstream of the SCC-A1 gene with varying lengths (set forth in SEQ ID Nos.:16–18). The mixed solutions after reaction were subjected to 0.8% agarose gel electrophoresis and the PCR products amplified specifically were collected. The gels were extracted using a QIAquick Gel extraction kit (QIAGEN Inc.). The results are collectively shown in Table 1.

TABLE 1

PCR Products

| DNA fragment | upstream primer | downstream primer | the length of PCR product (bp) |
|---|---|---|---|
| SEQ ID NO:16 | SEQ ID NO:10 | SEQ ID NO:15 | 250 |
| SEQ ID NO:17 | SEQ ID NO:11 | SEQ ID NO:15 | 500 |
| SEQ ID NO:18 | SEQ ID NO:12 | SEQ ID NO:15 | 1000 |
| SEQ ID NO:19 | SEQ ID NO:13 | SEQ ID NO:15 | 1997 |
| SEQ ID NO:20 | SEQ ID NO:14 | SEQ ID NO:15 | 3680 |

Basic vector (Nippon Gene Co., Ltd.), 0.1 µg, was subjected to restriction enzyme treatment by Mlu I (Takara Shuzo Co., Ltd.) and Bgl II (Takara Shuzo Co., Ltd.). The vector was mixed with the respective PCR products and ligation was carried out at 16° C. overnight by using a DNA ligation kit (Takara Shuzo Co., Ltd.).

By using the technique shown in Example 7, transformation was carried out and the plasmids were purified with a QIAGEN plasmid MINI kit.

The gene sequences of the plasmids into which the sequences set forth SEQ ID Nos.:16–20 had been inserted were identified with a DNA sequencer Type 310 (ABI Inc.). Following the aforementioned manipulations, the expression vectors having the upstream of the SCC-A1 gene with varying lengths (SEQ ID Nos.:16–18 as shown in FIG. 1) were prepared.

Example 9

Gene Expression Test I

Normal human epidermal keratinocytes (normal squamous epithelia) (Dainippon Pharmaceutical Co., Ltd.), SKG IIIa cells (squamous cell carcinoma), and ovarian cancer cells (SKOV3) (ATCC), which are non-squamous cell carcinoma cells, were inoculated in 12-well plates at $1.0 \times 10^6$ cells/well and grown overnight.

Five kinds of plasmid having SEQ ID Nos.: 16–20, a control vector having a SV40 promoter as positive control (Nippon Gene Co., Ltd.), and a basic vector having no promoter sequence as negative control were used in the respective tests. To each plasmid (1 µg) was added 6 µg of DOTAP liposomal transfection reagent solution (Boheringer-Mannheim Inc.), and it was allowed to stand at room temperature for 15 minutes to prepare a mixed transfection solution. For the addition group of epidermal keratinocytes, the mixed solution was added to 1 ml of a serum-free medium for normal human epidermal keratinocytes (Dainippon Pharmaceutical Co., Ltd.), while for the addition group of SKG IIIa cells and SKOV3 cells the mixed solution was added to 1 ml of an RPMI 1649 medium (GIBCO Inc.) containing 10% FCS (GIBCO Inc.). These were added to the 12-well plates on which the respective cells had been inoculated, and they were incubated at 37° C. under 5% $CO_2$ atmosphere. Six hours later the respective growth media were exchanged, and further incubated at 37° C. under 5% $CO_2$ atmosphere for 48 hours.

Forty eight hours later, a PicaGene Cell Culture Lysis reagent Luc (Nippon Gene Co., Ltd.) that had been diluted with PBS(-) solution was added at 200 µl per well to lyse the cells. The luciferase activity was determined using a PicaGene Luminescence Kit (Nippon Gene Co., Ltd.). Lumicounter 700 (Microtech Inc.) was used as a luminometer.

Figure 2:
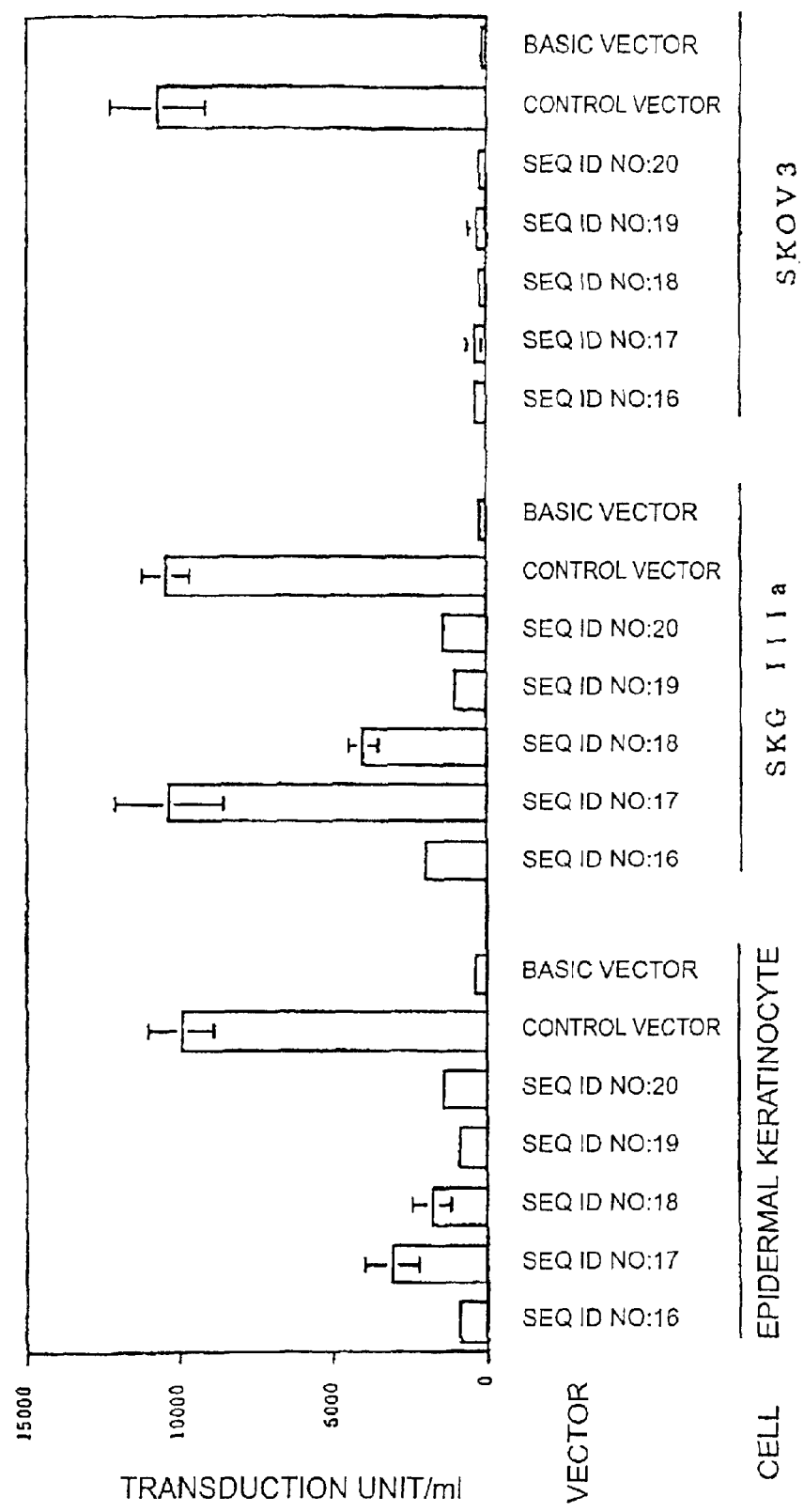
FIG. 2 is a graph showing a comparison of the levels of gene expression for cell species specific expression plasmids according to this invention in various cells.

The results are shown in FIG. 2. With respect to the five kinds of plasmid having the sequences set forth in SEQ ID Nos.:16–20, an increase in the luciferase activity was observed with epidermal keratinocytes and with SKG IIIa cells. On the other hand, almost no luciferase activity was detected in SKOV3 cells: at the same level as that of the basic vector having no promoter. With respect to the control vector having a SV40 promoter, the same high level of luciferase activity was detected in all the cells with no cell species specificity. This revealed that the five kinds of plasmid having SEQ ID Nos.:16–20 had the gene expression activity specific for squamous epithelium. Particularly, it was revealed that among the five kinds of plasmid having SEQ ID Nos.:16–20, the plasmids having the sequences set forth in SEQ ID Nos.:16–18 had strong gene expression activity. Further, it was found that the plasmid having the sequence set forth in SEQ ID NO:17 exhibited the strongest gene expression activity.

Example 10

Construction (II) of Expression Plasmids

To further investigate the specificity of SEQ ID NO: 17 which exhibited the strongest gene expression activity in Example 9, DNA fragments having the sequences set forth in SEQ ID Nos.:24–26 were prepared from the upstream of the SCC-A1 gene (SEQ ID NO:5), respectively, and the expression plasmids were constructed. Specifically, the expression plasmids were constructed by using the combinations of primers as shown in Table 2 according to the method similar to that of Example 8. Likewise, the upstream of the SCC-A2 gene (SEQ ID NO:6) was used as the template to construct DNA fragments (SEQ ID NO:27–32) having the same lengths as those of the DNA fragments having the sequences set forth in SEQ ID Nos.:16–18 and SEQ ID Nos.:24–26. The results are shown in Tables 2 and 3, respectively.

TABLE 2

PCR Products (derived from the upstream of the SCC-A1 gene)

| DNA fragment | upstream primer | downstream primer | the length of PCR product (bp) |
|---|---|---|---|
| SEQ ID NO 24 | SEQ ID NO:21 | SEQ ID NO:15 | 125 |
| SEQ ID NO:25 | SEQ ID NO:22 | SEQ ID NO:15 | 625 |
| SEQ ID NO:26 | SEQ ID NO:23 | SEQ ID NO:15 | 750 |

TABLE 3

PCR Products (derived from the upstream of the SCC-A2 gene)

| DNA fragment | upstream primer | downstream primer | the length of PCR product (bp) |
|---|---|---|---|
| SEQ ID NO:27 | SEQ ID NO:21 | SEQ ID NO:15 | 125 |
| SEQ ID NO:28 | SEQ ID NO:11 | SEQ ID NO:15 | 250 |
| SEQ ID NO:29 | SEQ ID NO:10 | SEQ ID NO:15 | 500 |
| SEQ ID NO:30 | SEQ ID NO:22 | SEQ ID NO:15 | 625 |
| SEQ ID NO:31 | SEQ ID NO:23 | SEQ ID NO:15 | 750 |
| SEQ ID NO:32 | SEQ ID NO:12 | SEQ ID NO:15 | 1001 |

Example 11

Gene Expression Test II

The expression plasmids having DNA fragments (SEQ ID NOs.:16–18) derived from the upstream of the SCC-A1 gene that had been prepared in Example 9, as well as the expression plasmids having DNA fragments (SEQ ID NOs.:24–26) derived from the upstream of the SCC-A1 gene and the expression plasmids having DNA fragments (SEQ ID NOs.:27–32) derived from the upstream of the SCC-A2 gene that had been prepared in Example 10 were determined for their gene expression activity.

Figure 3:
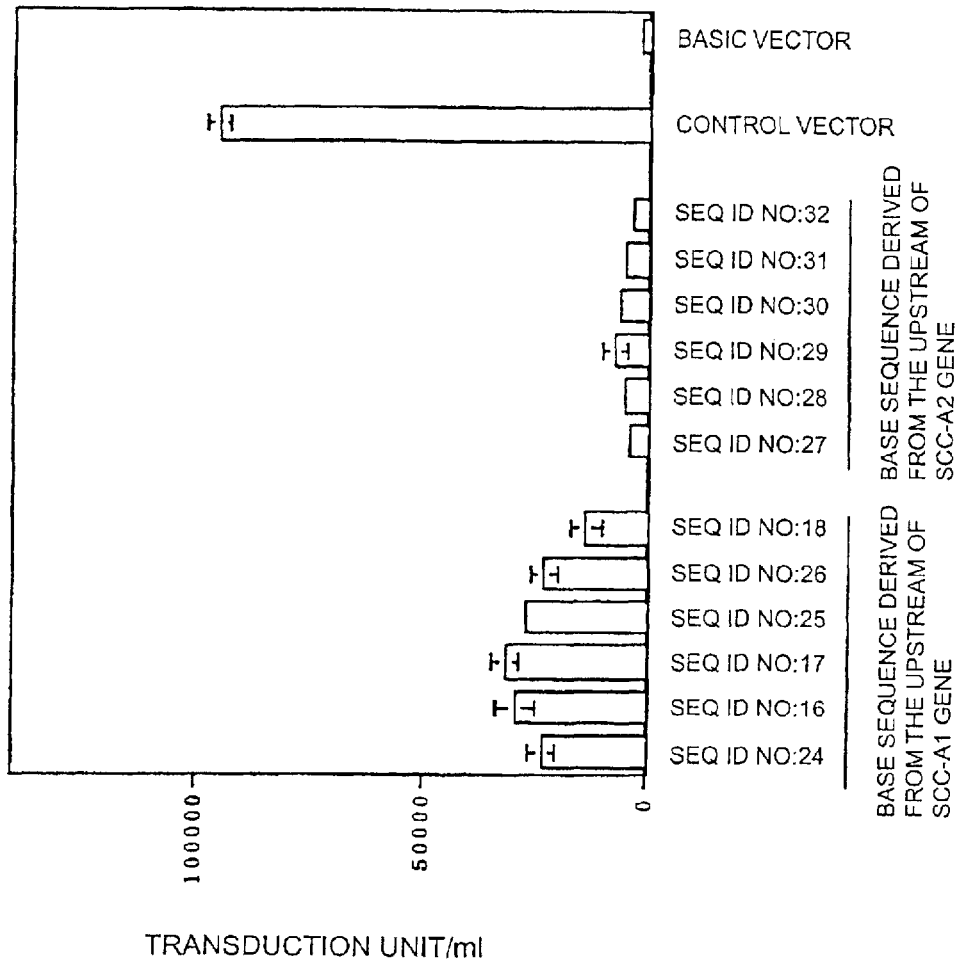
FIG. 3 is a graph showing a comparison of the levels of gene expression for cell species specific expression plasmids according to this invention in squamous epithelium.
Figure 4:
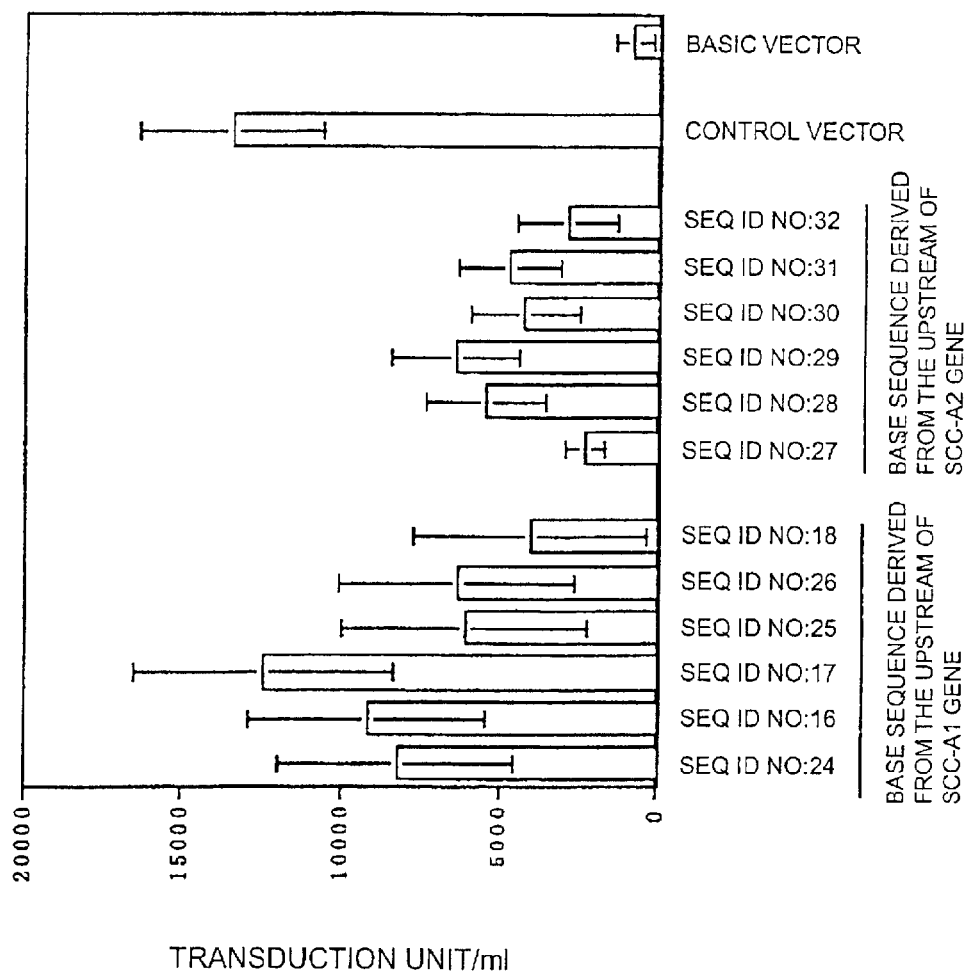
FIG. 4 is a graph showing a comparison of the levels of gene expression for cell species specific expression plasmids according to this invention in squamous cell carcinoma.
Figure 5:
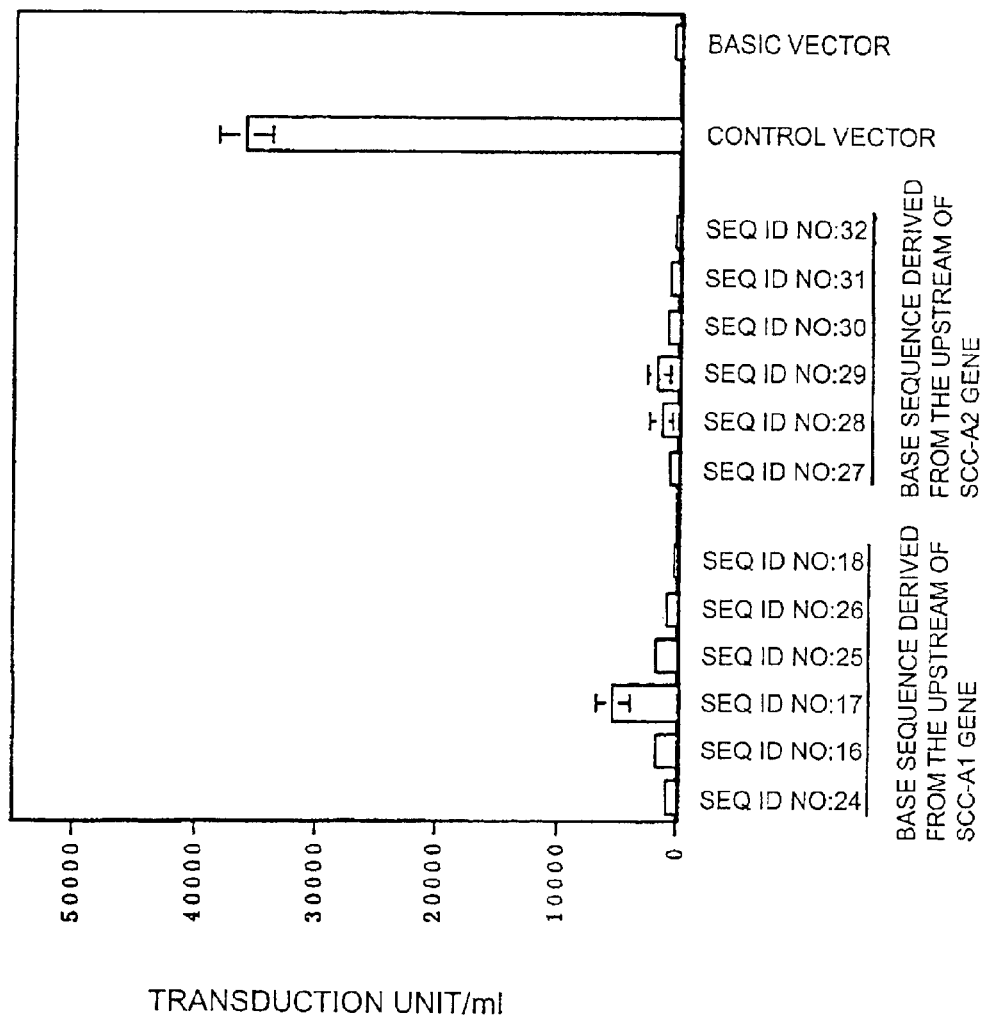
FIG. 5 is shows a graph showing a comparison of the levels of gene expression for cell species specific expression plasmids according to this invention in ovarian cancer cells.

The results are shown in FIGS. 3–5. FIG. 3 shows the gene expression activity of each expression plasmids in epidermal keratinocytes; FIG. 4 shows the gene expression activity of each expression plasmid in SKG IIIa cells; and FIG. 5 shows the gene expression activity of each expression plasmid in ovarian cancer cells, respectively.

With respect to the six kinds of plasmid having the DNA fragments derived from the upstream of the SCC-A1 gene (having the sequences set forth in SEQ ID NOs.:16–18 and 24–26) and the six kinds of plasmid having the DNA fragments derived from the upstream of the SCC-A2 gene (having the sequences set forth in SEQ ID NOs.:27–32), almost no luciferase activity was detected invariably in SKOV3 cells: at the same level as that of the basic vector having no promoter (FIG. 5). With respect to all the expression plasmids described above, an increase in the luciferase activity was observed with epidermal keratinocytes and with SKG IIIa cells as compared to the basic vector (FIGS. 3 and 4). Further, with respect to the expression plasmid of SEQ ID NO:17, the same high level of luciferase activity as that of the control vector having a SV40 promoter with no demonstrated cell species specificity was detected in SKG IIIa cells.

Thus, it was found that the twelve kinds of plasmid having the DNA fragments derived from the upstream of the SCC-A1 gene and from the upstream of the SCC-A2 gene all posses cell species specific, particularly squamous epithelium specific, gene expression activity. When both expression plasmid groups are compared, the former expression group (i.e., that which contain the base sequences derived from the upstream of the SCC-A1 gene) exhibited higher gene expression activity. It was further confirmed that the plasmid bearing a DNA fragment insert derived from the upstream of the SCC-A1 gene (having the sequence set forth SEQ ID NO:17) exhibits the strongest gene expression activity as compared to the other plasmids bearing DNA fragments other than that derived from the upstream of the SCC-A1 gene and to all the plasmids bearing DNA fragments derived from the upstream of the SCC-A2 gene.

Industrial Applicability

The base sequences for the expression of therapeutic genes according to this invention are those upstream the SCC-A gene and have the promoter function of directing the expression of certain genes specifically to squamous epithelia.

According to this invention, the therapeutic genes can be specifically expressed in squamous epithelia by introducing the therapeutic genes to the downstream of such base sequences as mentioned above.

Moreover, according to this invention, the medicaments for gene therapy where therapeutic genes are introduced to the downstream of the above-mentioned base sequences can be obtained that are capable of directing the expression of the therapeutic genes specifically to squamous epithelia.

What is claimed is:

1. An isolated base sequence for the expression of a therapeutic gene, said sequence comprising any of (a), (b), (c) or (d) below, said base sequence containing the sequence set forth in SEQ ID NO:24, and capable of directing the expression of the therapeutic gene specifically to squamous epithelium:

(a) the base sequence set forth in SEQ ID NO:1 in the Sequence Listing;

(b) the base sequence set forth in SEQ ID NO:18 in the Sequence Listing;

(c) the base sequence set forth in SEQ ID NO:17 in the Sequence Listing; or (d) the base sequence set forth in SEQ ID NO:16 in the Sequence Listing.

2. A medicament for gene therapy comprising a therapeutic gene operably linked to the base sequence according to claim 1, capable of directing expression of the therapeutic gene specifically to squamous epithelium.

3. An isolated base sequence according to claim 1, wherein said base sequence is the base sequence set forth in the SEQ ID NO:1 in the Sequence Listing.

4. An isolated base sequence according to claim 1, wherein said base sequence is the base sequence set forth in the SEQ ID NO:18 in the Sequence Listing.

5. An isolated base sequence according to claim 1, wherein said base sequence is the base sequence set forth in the SEQ ID NO:17 in the Sequence Listing.

6. An isolated base sequence according to claim 1, wherein said base sequence is the base sequence set forth in the SEQ ID NO:16 in the Sequence Listing.

* * * * *